(12) United States Patent
Li et al.

(10) Patent No.: US 10,620,197 B2
(45) Date of Patent: Apr. 14, 2020

(54) MAGNETIC MICROCHIP HAVING GRAPH CODE AS WELL AS PREPARATION METHOD AND APPLICATION THEREOF

(71) Applicant: Suzhou Institute of Nano-Tech and Nano-Bionics (Sinano), Chinese Academy of Sciences, Sip Suzhou (CN)

(72) Inventors: Jiong Li, Sip Suzhou (CN); Kexiao Zheng, Sip Suzhou (CN); Chao Chen, Sip Suzhou (CN)

(73) Assignee: Suzhou Institute of Nano-Tech and Nano-Bionics (Sinano), Chinese Academy of Sciences, Suzhou (CN)

( * ) Notice: Subject to any disclaimer, the term of this patent is extended or adjusted under 35 U.S.C. 154(b) by 56 days.

(21) Appl. No.: 15/777,818

(22) PCT Filed: Apr. 14, 2017

(86) PCT No.: PCT/CN2017/080595
§ 371 (c)(1),
(2) Date: May 21, 2018

(87) PCT Pub. No.: WO2017/177971
PCT Pub. Date: Oct. 19, 2017

(65) Prior Publication Data
US 2019/0120831 A1    Apr. 25, 2019

(30) Foreign Application Priority Data
Apr. 14, 2016  (CN) .......................... 2016 1 0230223

(51) Int. Cl.
*G01N 33/551* (2006.01)
*G01N 33/543* (2006.01)
(Continued)

(52) U.S. Cl.
CPC ......... *G01N 33/54326* (2013.01); *B81B 1/00* (2013.01); *C12Q 1/6816* (2013.01);
(Continued)

(58) Field of Classification Search
None
See application file for complete search history.

(56) References Cited

U.S. PATENT DOCUMENTS

2005/0227252 A1* 10/2005 Moon .............. G01N 33/54313
435/6.18

FOREIGN PATENT DOCUMENTS

CN      101693514 A      4/2010
CN      102936754 A      2/2013
(Continued)

OTHER PUBLICATIONS

International Search Report of international priority application PCT/CN2017/080595.

*Primary Examiner* — Christopher L Chin
(74) *Attorney, Agent, or Firm* — Wang Law Firm, Inc.

(57) ABSTRACT

The present application discloses a magnetic microchip having a graph code as well as a preparation method and application thereof. The magnetic microchip comprises: a graph code comprising more than one opaque microstructure mainly consisting of colloid aggregates formed by aggregating magnetic solid particles, wherein adjacent magnetic solid particles are isolated at least by an organic molecule and/or an inorganic molecule; and a transparent encapsulating structure at least used for wrapping the opaque microstructure. The magnetic microchip of the present application is prepared by adopting a micromachining process and has high in machining precision and repeatability, the size difference between different batches or between different individuals at the same batch can be ignored, use is conve- (Continued)

nient, and accuracy of a detection result can be effectively ensured, thereby greatly improving analysis quality.

28 Claims, 9 Drawing Sheets

Specification includes a Sequence Listing.

(51) Int. Cl.
*B81B 1/00* (2006.01)
*C12Q 1/6816* (2018.01)
*G01N 33/553* (2006.01)
*C12Q 1/6834* (2018.01)

(52) U.S. Cl.
CPC . *G01N 33/54346* (2013.01); *G01N 33/54393* (2013.01); *G01N 33/553* (2013.01); *C12Q 1/6834* (2013.01)

(56) References Cited

FOREIGN PATENT DOCUMENTS

| | | | |
|---|---|---|---|
| CN | 104307097 | A | 1/2015 |
| WO | 2011014879 | A2 | 2/2011 |
| WO | 2016198954 | A1 | 12/2016 |

* cited by examiner

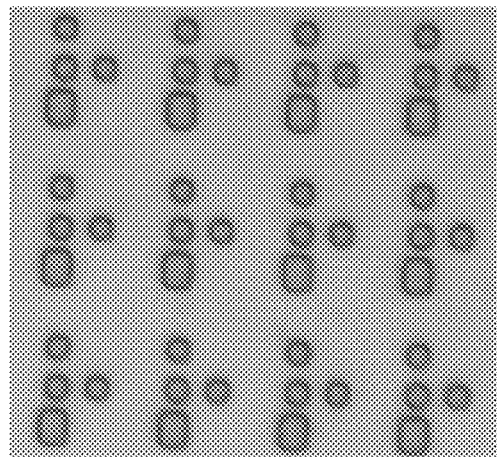
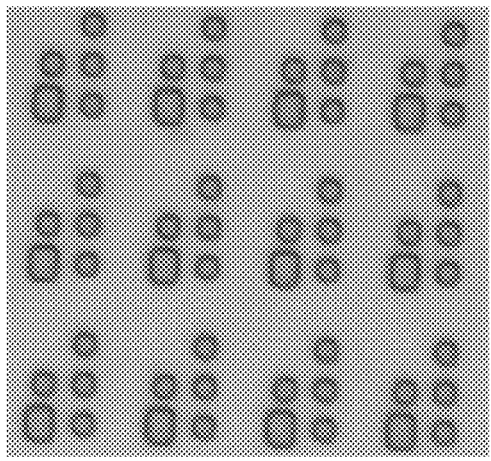
FIG.3a  FIG.3b
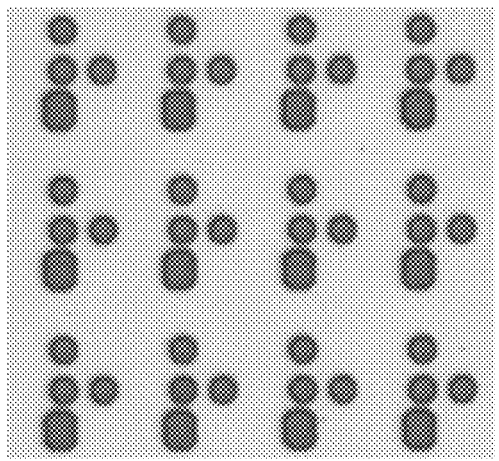
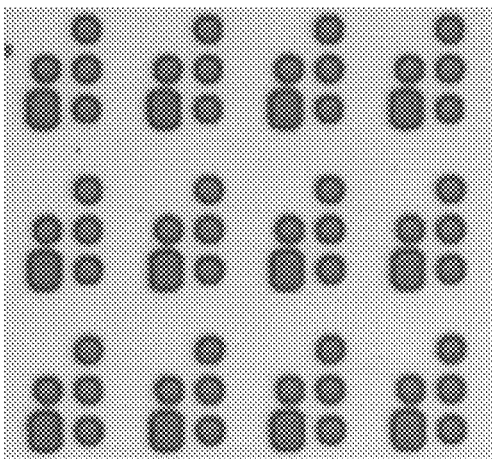
FIG.4a  FIG.4b

MAGNETIC MICROCHIP HAVING GRAPH CODE AS WELL AS PREPARATION METHOD AND APPLICATION THEREOF

TECHNICAL FIELD

The present application relates to a suspension microchip, and particularly relates to a magnetic microchip having a graph code and a preparation process thereof.

BACKGROUND

Complicated vital activities often result from synergism of a group of biomolecules serving as core execution elements. Fingerprints of many diseases remained in a molecular level are often decided by multiple biomarkers. In other words, "pattern characteristics" presented by multiple marker sets have stronger correlation with specific physiological and pathological phenomena than those of a single molecule. It is estimated (Nature, 2011.469(7329):p. 156-157) that thousands of biomarkers have been described in about 15 millions of documents, among them, there are about 100~200 common markers approved to be clinically used. Relative to a single biomarker, a biomarker set consisting of multiple characteristic molecules is capable of providing crucial instruction information for clinical works in the aspects of early diagnosis, disease subtypes, risk predication, drug selection, disease course monitoring, prognosis estimation and the like in a more comprehensive, precise and efficient manner. In life science research, analysis on multiple biomarkers are often used for disclosing an action mechanism of a biological signal path. In addition, a large number of multiplex biomarker detection is introduced in modern pharmaceutical research for evaluation of drug efficacy and toxicity. As precise medicine age comes, precise quantification on multiple biomarkers in a large number of specimens will increasingly become an indispensable mainstream analysis task in the fields of modern diagnostics, therapeutics, drug research and development, translational medicine and the like.

A multiplex biological detection technology is a powerful tool satisfying a large-scale parallel biological analysis demand. Undoubtedly, although some classical single detection technologies (such as enzyme-linked immune assay, immunoblotting and real-time quantitative PCR) can also complete quantification on multiple analytes through a large amount of complicated operations, it is still difficult to overcome the following obstacles: respective sampling directed to different analytes leads huge logistic burden (sample collection, record, storage, transportation and the like); the same specimen must be allocated to multiple different detections, but its limited volume difficulty considers all the detections (especially oncology department and paediatric specimens); the whole set of detection is expensive in cost and huge in manpower consumption; timely completion of all detection items faces a huge pressure. With HPV (human papilloma virus) detection as an example, 14 high-risk type HPVs, affirmed by WHO (World Health Organization) and IRAC (International Agency for Research on Cancer), among about more than 30 HPVs that have been discovered at present and can infect human genital tract mucosa, can easily lead generation of cervical cancer. Considering necessary control and 3 repetitions, about 60 routine PCR (polymerase Chain Reaction) reactions need to be done for the whole detection, burdens of subsequent cost and operation amount make it difficulty popularized in clinic. Facing an increasing automated high-throughput multiplex assay demand in clinic diagnosis and medicine research and development application, a single detection mode of a routine technology has become a bottleneck restricting data output efficiency. However, for multiplex assay, all the detections can be completed in once operation without separating specimens, thereby not only greatly reducing the consumption of detection and shortening the detection period, but also facilitating standardization of sample treatment and automation of measurement methods.

A suspension chip is a technology utilizing a sorting coding microchip suspending in a liquid phase as a reaction and signal detection carrier. Its core characteristic lies in that the used microsphere has a code that is unique and can be identified by a machine. At present, the most widely applied suspension microchip technology mainly includes a fluorescence-coded microsphere technology and a bar code magnetic bead technology, but these suspension microchips generally have the deficiencies of complicated preparation process, high cost and the like.

The inventor of the present application also once developed a coding graph suspension chip based on a high-refection multi-layer dielectric stacking plated film, optical contrast between the code and a base mainly depends on a reflection effect of a high-reflection plated film. Under the illumination conditions of common white light, it is needed to perform film system design aiming at light intensity distribution of a specific light source, and it is need to perform high-precision plating process many times to achieve an expected reflection effect, so process difficulty is large and manufacturing cost is high.

SUMMARY

The main objective of the present application is to provide a magnetic microchip having a graph code as well as a preparation method and application thereof to overcome the deficiencies in the prior art.

In order to achieve the above objective of the disclosure, the technical solution adopted by the present application includes:

An embodiment of the present application provides a preparation method of a microchip having a graph code, comprising:

providing a transparent substrate layer;

applying a film formed by cured ferrofluid on the transparent substrate layer;

at least removing a portion of base carrying liquid in the film so that at least a portion of the film is cured to form a ferrofluid layer;

machining the ferrofluid layer to form an opaque microstructure as the graph code;

wrapping the opaque microstructure with a transparent material to form the magnetic microchip.

In some preferred embodiments, the preparation method comprises:

coating the ferrofluid on the transparent substrate layer to form the film, heating to remove at least a portion of base carrying liquid in the film, thereby forming the ferrofluid layer.

An Embodiment of the present application also provides a magnetic microchip having a graph code, comprising:

the graph code comprising more than one opaque microstructure mainly consisting of colloid aggregates formed by aggregating magnetic solid particles, wherein adjacent magnetic solid particles are isolated at least by an organic molecule and/or an inorganic molecule;

and a transparent encapsulating material at least used for wrapping the opaque microstructure.

In some preferred embodiments, all the opaque microstructures in each magnetic microchip are combined to form one group of two-dimensional graphs.

Preferably, two-dimensional graphs contained in at least two different magnetic microchips are geometrically distinguished.

Further, the opaque microstructure is formed by the ferrofluid after at least a portion of base carrying liquid is removed. Preferably, the organic molecule and/or the inorganic molecule comprises a surfactant molecule and/or a base carrying liquid molecule derived from the ferrofluid.

An embodiment of the present application also provides use of the microchip having the graph code.

Compared with the prior art, the present application has the advantages that:

(1) The magnetic microchip having the graph code provided by the present application can be prepared by adopting a micromachining technology, and is high in machining precision and repeatability, the size difference between different batches or between different individuals at the same batch can be ignored, and the accuracy of detection result can be effectively ensured, and therefore analysis quality can be greatly improved (for example, data repeatability).

(2) Magnetism of the magnetic microchip having the graph code provided by the present application comes from cured ferrofluid, this manner of introducing a magnetic material is not only economic but also extremely simple and practicable, precise equipment is not needed, and treatment time of each wafer is controlled in a few minutes.

(3) The magnetic microchip having the graph code provided by the present application has a smaller size, for example, an approximately traditional microsphere for biological analysis, and both of a suspension capability of the microsphere in liquid and reaction dynamics of its surface more facilitate capture of analytes, so as to realize higher detection sensitivity and specificity, and due to small size of a single magnetic microchip, micromachining manufacturing is facilitated, yield is higher, and cost is lower.

(4) The magnetic microchip having the graph code provided by the present application preferably adopts silicon dioxide as a substrate, and functional ligands for capturing analyte molecules, such as various molecule probes, can be conveniently connected without additional biophile modification, and an application range of the magnetic microchip in the field of biology is expanded.

BRIEF DESCRIPTION OF THE DRAWINGS

In order to more clearly illustrate technical solutions in embodiments of the present application or in the prior art, drawings required to be used in description of embodiments or the prior art will be simply introduced below, apparently, drawings in the following description are only some embodiments of the present application, and persons of ordinary skill in the art may also obtain other drawings according to these drawings without creative efforts.

FIG. 3a-FIG. 3b are metallographic microphotographs of two ferrofluid layers whose surfaces are covered with patterned etch masks in one embodiment of the present application, respectively.

FIG. 4a-FIG. 4b are metallographic microphotographs of two ferrofluid layers after patterning and etching in one embodiment of the present application, respectively.

DESCRIPTION OF THE EMBODIMENTS

Figure 1:
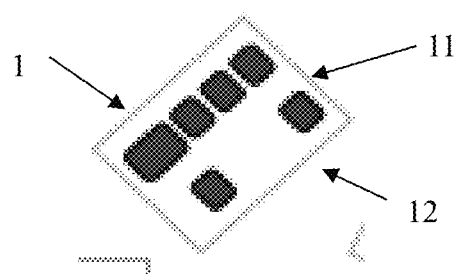
FIG. 1 is a front view of a magnetic microchip having a graph code in one typical embodiment of the present application.

In order to make objectives, technical solutions and advantages of the present application more clear, embodiments of the present application will be described in detail below in combination with drawings. Examples of these preferable embodiments are exemplified in drawings. Embodiments of the present application shown in drawings and according to description of drawings are merely exemplary, and the present application is not limited to these embodiments.

Here, it is also noted that in order to prevent the present application from being bleared due to unnecessary details, in the drawings, structures and/or treatment steps closely associated with solutions according to the present application are only illustrated, and other details that have little relation with the present application are omitted.

One aspect of embodiments of the present application provides a preparation method of a magnetic microchip having a graph code, comprising:

providing a transparent substrate layer;

applying a film formed by ferrofluid on the transparent substrate layer;

at least removing a portion of base carrying liquid in the film so that at least a portion of the film is cured to form a ferrofluid layer;

machining the ferrofluid layer to form an opaque microstructure as the graph code;

wrapping the opaque microstructure with a transparent material to form the magnetic microchip.

In some preferred embodiments, the preparation method comprises:

coating the ferrofluid on the transparent substrate layer to form the film;

heating to remove at least a portion of base carrying liquid in the film, thereby forming the ferrofluid layer.

Where, temperatures, time and the like of heating are easily determined by those skilled in the art according to the content and type of the base carrying liquid in the ferrofluid, a proportion of the base carrying liquid needing to be removed and the like.

In the present application, the ferrofluid comprises magnetic solid particles, a surfactant and a base carrying liquid, the base carrying liquid being sufficient to disperse the magnetic solid particles together with the surfactant to form a colloid suspension.

More further, the ferrofluid is a stable colloidal liquid formed by mixing magnetic solid particles having a diameter of nano scale (10 nm below), the base carrying liquid (also referred to as a medium) and the surfactant, and the ferrofluid has no magnetic attraction when in static state, and exhibits magnetism only when magnetic field action is applied. Where, the base carrying liquid serve as a continuous phase, and the magnetic solid particles serve as a non-continuous phase or a dispersion phase.

More preferably, the magnetic solid particle has a particle size of 1 nm~1000 nm.

Where, the ferrofluid may select various proper types known in the art, for example, may be selected from any one or a combination of more than two of ferrite series ferrofluid, metal series ferrofluid and iron nitride series ferrofluid, but is not limited thereto.

Further, the material of the ferrite series ferrofluid may comprise any one or a combination of more than two of $Fe_3O_4$, $\gamma\text{-}Fe_2O_3$ and $MeFe_2O_4$, wherein, Me is at least selected from Co, Ni, Mn or Zn and the like, but is not limited thereto;

Further, the metal series ferrofluid comprises metal microparticles formed by any one or a combination of more than two of Ni, Co and Fe, but is not limited thereto.

The ferrofluid described in the present application can be prepared by a grinding method, a peptization method, a thermal decomposition method, a discharge method and other manners known in the art (see "Ferrofluid and Application Thereof", mechanical engineering, No. 1, 1991).

Further, in the ferrofluid layer of the present application, adjacent magnetic solid particles are isolated at least by an organic molecule and/or an inorganic molecule derived from the ferrofluid.

Preferably, the organic molecule and/or the inorganic molecule comprises a surfactant molecule and/or a base carrying liquid molecule derived from the ferrofluid.

As one of preferred embodiments, the ferrofluid layer contains 50V/V %~99V/V % of magnetic solid particles, 0.5V/V %~50V/V % of surfactant molecule and 0.5V/V %~50V/V % of base carrying liquid molecule. Preferably, the ferrofluid layer contains 75V/V %~99V/V % of magnetic solid particles, 0.5V/V %~15V/V % of surfactant molecule and 0.5V/V %~15V/V % of base carrying liquid molecule.

Where, the ferrofluid layer formed by the ferrofluid in which a portion of base carrying liquid is removed can also be regarded as a cured ferrofluid which still maintains superparamagnetism and other characteristics of the ferrofluid.

More preferably, the opaque microstructure has a thickness of 10 nm~1000 nm. If the thickness of the opaque microstructure is extremely large, the amount of the ferrofluid is increased, disadvantageous effects of extending machining time of a ferrofluid chip, increasing the whole thickness of the chip and the like are also brought, and if the thickness of the opaque microstructure is extremely small, the opaque microstructure has a potential to lack desired light obstructing capability, that is, it is possible that a transparent part and an opaque part of the magnetic microchip in an optical channel cannot be extremely clear to distinguish, so that the graph code cannot be accurately identified.

In some embodiments, the preparation method may also comprise: providing a patterned etch mask on the ferrofluid layer and etching the ferrofluid layer to form the opaque microstructure.

In some specific embodiments, the preparation method may comprise: etching the ferrofluid layer by at least adopting any one or a combination of more than two of machining, a dry etching process and a wet etching process, thereby forming the opaque microstructure.

In some specific embodiments, the preparation method may comprise:

providing a sacrificial layer on a base, forming a transparent substrate layer on the sacrificial layer, uniformly coating the film formed by the ferrofluid on the transparent substrate layer.

In some specific embodiments, the preparation method may comprise: dividing a formed device according to a setting manner after the opaque microstructure is coated with a transparent material, then removing the sacrificial layer to obtain more than two pieces of magnetic microchips independent from each other.

Where, a manner by which the ferrofluid is uniformly coated on the transparent substrate layer can be numerous manners, such as blade coating, spinning, spraying and printing.

Where, a division method can be mechanical cutting, laser scribing or the like.

For the above sacrificial layer, other liquid agents which are capable of dissolving these materials in a chemical or physical manner but not damaging a transparent material layer and a material layer sufficiently opaque to visible light can also be adopted to perform corresponding removal operations. In addition, removal of the sacrificial layer by virtue of mechanical stripping, stress stripping or other technical means commonly used by those skilled in the art cannot be excluded either. In the present application, a liquid agent dissolution manner is preferably adapted to remove the sacrificial layer, for example, for a sacrificial layer formed by a photoresist, the liquid agent comprises acetone solution; for a sacrificial layer formed by aluminum, the liquid agent comprises diluted hydrochloric acid. And for some high molecular materials, they are completely removed via corresponding organic solvents.

For a manner that the sacrificial layer is removed by virtue of dissolution, the sacrificial layer and the base can be removed under the condition that the magnetic microchip is not substantially damaged.

In some specific embodiments, the preparation method may comprise: forming a metal thin layer, serving as a sacrificial layer, on the base through a metal plating process.

Preferably, the material of the metal thin layer may comprise aluminum but is not limited thereto.

More preferably, the transparent material wrapping the opaque microstructure has a visible light transmittance of 50% or more, preferably 90% or more.

More preferably, the transparent material wrapping the opaque microstructure has a thickness of 100 nm~5000 nm.

Further, the material of the transparent substrate layer and the transparent material are preferably selected from bioinert transparent materials, for example, can adopt silicon dioxide, but is not limited thereto.

Further, for the form of the magnetic microchip, it can be of particle shape (for example sphere or rectangle), tablet shape and the like. And preferably, any one of length, width and height or a diameter of the magnetic microchip is 1 μm~1000 μm.

But especially preferably, the magnetic microchip has a flat two-dimensional surface-shaped structure, and this form of magnetic microchip is superior to other forms of magnetic microchips in the aspects of machining convenience and the like.

Further preferably, the magnetic microchip has a length and a width of no more than 100 μm and a thickness of no more than 2 μm. More further preferably, the magnetic microchip has a length and a width of 10 μm~50 μm and a thickness of 0.5 μm~2 μm. If the size of the magnetic microchip is extremely large, it is not prone to exhibiting a suspension state in a liquid phase system, and if the size of the magnetic microchip is extremely small, on one hand, the machining difficulty is improved, on the other hand, it is not beneficial for precise imaging in an optical system.

In some specific embodiments, the preparation method specifically may comprise the following steps:

providing a sacrificial layer on a base, forming a transparent substrate layer on the sacrificial layer, uniformly coating the film formed by ferrofluid on the transparent substrate layer, at least removing a portion of base carrying liquid in the film so that at last a portion of film is cured form a ferrofluid layer, providing a patterned etch mask on the ferrofluid layer, and etching the ferrofluid layer to form the opaque microstructure;

wrapping the opaque microstructure with a transparent material, then dividing a formed device according to a setting manner, and then removing the sacrificial layer to obtain more than two pieces of magnetic microchips independent from each other.

The opaque microstructure is coated with the transparent material, then the formed device is divided in a setting manner, subsequently, the sacrificial layer is removed to obtain more than two magnetic microchips independent from each other.

The above base may adopt various kinds of organic and inorganic materials or composite materials thereof and the like, for example Si, glass and metal but not limited thereto.

In some specific embodiments, the preparation method may comprise: by adopting a centrifugal spinning or other manners, uniformly coating ferrofluid on a transparent substrate layer to form a film, then removing a portion of base carrying liquid in the film by adopting a heating manner, thereby forming the ferrofluid. In such embodiments, two processes namely centrifugal spinning and heating are successively adopted to function as removing the base carrying liquid (generally organic solvent) of the ferrofluid, the former makes the base carrying liquid thrown away from the surface of a wafer, and the later makes it volatilized. After being cured, the magnetic solid particles form colloidal aggregates, but connected surfactant molecules and adsorbed base carrying molecules on their surfaces make the magnetic solid particles still kept in a separation state, so that the superparamagnetism of the ferrofluid is retained.

Of course, in some enforceable solutions, the ferrofluid can be directly applied to a transparent base through a silk-screen printing or other manners to form a film having a set graph, and then the film is directly dried, thereby forming the opaque microstructure. But this manner needs precise control.

In the present application, the above graph code can be identified after optical imaging under the illumination of visible light, and can be converted into a digital code according to a preset rule or procedure for denoting an identity (type) of the microchip, and numerous different types of magnetic microchips are coded by being prepared into different graphs.

In the present application, a graph code contained in each magnetic microchip may comprise at least one group of two-dimensional graphs formed by combining at least two opaque microstructures.

Preferably, all the opaque microstructures in each magnetic microchip are combined to form one group of two-dimensional graphs.

Further preferably, two-dimensional graphs contained in at least two different magnetic microchips are geometrically distinguished.

Where, the "geometrical distinguishing" refers to a fact that none of any operations, such as translation, rotation and overturning, enables any two groups of graphs to be completely coincided.

In some preferred embodiments, the preparation method may also further comprise: connecting a capture substance for specifically capturing a target substance on the surface of the magnetic microchip. Preferably, the capture substance is selected from an organic compound and/or an inorganic compound. For example, the organic compound comprises any one or a combination of more than two of protein, an antibody, a polypeptide and nucleic acid, and is not limited thereto.

In some preferred embodiments, the preparation method may also further comprise: connecting a hydrophilic group on the surface of the magnetic microchip. Preferably, the source substance of the hydrophilic group comprises any one or a combination of more than two of PEG, glucan, chitosan and alginate, and is not limited thereto.

Further, the magnetic microchip of the present application can be prepared by a complementary metal-oxide semiconductor (CMOS) compatible process in a semi-conductor process facility.

In summary, the magnetic microchip of the present application can be prepared by adopting the above micromachining process, which is not only economic but also extremely simple and practicable (precise equipment is not needed, and the treatment time of each wafer can be controlled in a few minutes), meanwhile, its machining precision and repeatability are high, and the size difference between different batches or different individuals in the same batch can be ignored, in such a way, the accuracy of a detection result can be guaranteed, and thus analysis quality can be guaranteed (for example data repeatability).

Another aspect of embodiments of the present application provides a magnetic microchip having a graph code, comprising:

the graph code comprising more than one opaque microstructure mainly consisting of colloid aggregates formed by aggregating magnetic solid particles, wherein adjacent magnetic solid particles are isolated at least by an organic molecule and/or an inorganic molecule;

and a transparent encapsulating material at least used for wrapping the opaque microstructure.

Further, the graph code comprises at least one group of two-dimensional graphs formed by combining at least two opaque microstructures.

That is, in the magnetic microchip, the graph code is a two-dimensional graph formed by using the opaque microstructure as a basic unit.

Preferably, all the opaque microstructures in each magnetic microchip are combined to form one group of two-dimensional graphs.

Further, under the illumination of transmission lights of a microscope light field, the transparent encapsulating material body of the magnetic microchip of the present application is bright, but a part of the opaque microstructure is dark and gloomy, and there are good optical contrast therebetween.

Especially preferably, two-dimensional graphs contained in at least two different magnetic microchips are geometrically distinguished. Where, the "geometrical distinguishing" refers to a fact that none of any operations, such as any translation, rotation and overturning, enables any two groups of graphs to be completely coincided.

In the present application, a plurality of groups of geometrically distinguishable graphs can be generated by changing an arrangement manner (including but not limited to size, shape, position and the like of the opaque microstructure) of the opaque microstructure. Thus, each group of graphs can be regarded as a unique code. An identity of each magnetic microchip can be quickly and accurately determined as long as a microimaging apparatus is used under the condition of light field illumination to obtain a picture of the magnetic microchip and then machine decoding is carried out on the picture utilizing image identification software.

More preferably, the magnetic microchip has a flat two-dimensional surface-shaped structure.

Further, the opaque microstructure is formed by ferrofluid after at least a part of base carrying liquid is removed. In other words, the opaque microstructure can be actually regarded as a cured ferrofluid which still maintains superparamagnerism and other characteristics of ferrofluid. And due to opacity of the cured ferrofluid itself, the microstructure formed by the cured ferrofluid is opaque as well.

Moreover, for the opaque microstructure, the above curved ferrofluid is wrapped inside the transparent encapsulating material, and thus when the cured ferrofluid is dispersed into a liquid phase system such as biochemical reaction, oxidization and other chemical reactions affecting its paramagnetism cannot be generated.

Preferably, the organic molecule and/or the inorganic molecule comprise(s) a surfactant molecule and/or a base carrying liquid molecule derived from ferrofluid.

For the composition of the ferrofluid, it is described as above, and duplicate discussion will be omitted.

Further, in the opaque microstructure, adjacent magnetic solid particles are isolated at least by an organic molecule and/or an inorganic molecule derived from the ferrofluid. Preferably, the organic molecule and/or the inorganic molecule comprises a surfactant molecule and/or a base carrying liquid molecule derived from ferrofluid.

In some preferred embodiments, the opaque microstructure contains 50V/V %~99V/V % of magnetic solid particles, 0.5V/V %~50V/V % of surfactant molecule and 0.5V/V %~50V/V % of base carrying liquid molecule; especially preferably, the opaque microstructure contains 75V/V %~99V/V % of magnetic solid particles, 0.5V/V %~15V/V % of surfactant molecule and 0.5V/V %~15V/V % of base carrying liquid molecule; more preferably, the opaque microstructure contains 80V/V %~99V/V % of magnetic solid particles, 0.5V/V %~10V/V % of surfactant molecule and 0.5V/V %~10V/V % of base carrying liquid molecule. In such embodiments, the magnetic solid particles can be aggregated closely enough so that the opaque microstructure has desired light obstruction capability, and influence on its superparamagnetism due to aggregation of the magnetic solid particles is not caused.

In some preferred embodiments, the opaque microstructure has a thickness of 10 nm~1000 nm. If the thickness of the opaque microstructure is extremely large, the amount of the ferrofluid is increased, and disadvantageous influences of extending the machining time of the ferrofluid chip and the like can also be brought, and if the thickness of the opaque microstructure is extremely small, the opaque microstructure has a potential to lack desired light obstruction capability, that is, it is possibly that a transparent part and an opaque part of the magnetic microchip in an optical channel cannot be extremely clear to distinguish, so that the graph code cannot be accurately identified.

Especially preferably, through allowing the opaque microstructure to have substance composition and thickness described in the above preferred embodiments, the opaque structure still has good light obstruction performance under the condition of a few amount of ferrofluid.

Further, for the form of the magnetic microchip, it can be of particle shape (for example sphere or rectangle), tablet shape or the like. And preferably, any one of length, width and height or a diameter of the magnetic microchip is 1 μm~1000 μm.

But especially preferably, the magnetic microchip has a flat two-dimensional surface-shaped structure, this form of magnetic microchip is superior to other forms of magnetic microchips in the aspects of machining convenience and the like.

Further preferably, the magnetic microchip has a length and a width of no more than 100 μm and a thickness of no more than 2 μm. More further preferably, the magnetic microchip has a length and a width of 10 μm~50 μm and a thickness of 0.5 μm~2 μm. If the size of the magnetic microchip is extremely large, it is not prone to exhibiting a suspension state in a liquid phase system, and if the size of the magnetic microchip is extremely small, on one hand, its machining difficulty is improved, on the other hand, it is not beneficial for performing precise imaging in an optical system.

In the present application, the suspension capability of the magnetic microchip having the above preferable sizes in the liquid phase system and reaction dynamics of its surface are both more beneficial for capturing analytes, thereby achieving higher detection sensitivity and specificity, and on the other hand, micromachining is facilitated, so yield is high, and cost is low.

Preferably, the transparent encapsulating material wrapping the opaque microstructure has a visible light transmittance of 50% or more.

Preferably, the transparent encapsulating material wrapping the opaque microstructure has a thickness of 100 nm~5000 nm.

Further preferably, the transparent encapsulating material is selected from bioinert transparent materials, for example, silicon dioxide can be adopted, in such a way, the magnetic microchip of the present application does not generate interference or pollution in samples derived from various biological sources, and various biomolecules are immobilized on its surface through a coupling chemical method known in the art so as to react with a specific target molecule and a molecular marker in the sample, so that a physical signal that can be detected is generated on the surface of the chip to achieve an objective of detection.

In some preferred embodiments, the surface of the magnetic microchip is also connected with a capture substance for specifically capturing a target substance. Preferably, the capture substance is selected from an organic compound and/or an inorganic compound, for example, the organic compound may comprise any one or a combination of more than two of protein, an antibody, a polypeptide and nucleic acid, but is not limited thereto.

In some preferred embodiments, the surface of the magnetic microchip is also connected with a hydrophilic group to provide richer coupling sites, inhibit specific adsorption and improve hydraulic performance of the chip. Preferably, the source substance of the hydrophilic group may comprise any one or a combination of more than two of PEG; glucan, chitosan and alginate, but is not limited thereto.

The magnetic microchip of the present application contains cured ferrofluid having superparamagnetism, and thus, when in application, the magnetic microchip moves to a designated position of a container of the liquid phase system through application of a magnetic field and is fixed at this position by a magnetic force, thereby achieving solid-liquid separation of a suspension. Under such a state, liquor relieving, liquor change, washing and other operations can be carried out without leading loss of the magnetic microchip. After the applied magnetic field is withdrawn, paramagnetic materials loss magnetism and have no mutual attraction to difficulty generate aggregation, and the magnetic microchips can be dispersed and resuspend in the liquid phase system through low-strength mechanical oscillation or agitation.

Referring to FIG. 1, which illustrates a front view of a magnetic microchip according to the present application. The magnetic microchip 1 comprises an opaque microstructure 11 formed by the above cured ferrofluid and a transparent encapsulating material 12 wrapping the opaque microstructure. Where, a plurality of opaque microstructures 11 are combined to form one group of two-dimensional graphs, and the two-dimensional graph serves as a graph code. When the magnetic microchip is illuminated by microscope light field transmission light, the transparent encapsulating material body is bright, and a part of opaque microstructure is dark and gloomy, and there is good optical contrast therebetween. Then, many groups of geometrically distinguishable graphs can be generated by changing the arrangement manner (for example, the size, shape, position and the like of the opaque microstructure) of the opaque microstructure. Thus, each group of graphs can be regarded as a specific graph code. As described above, an identify of each magnetic microchip can be quickly and accurately determined as long as a microimaging apparatus is used under the illumination condition of a light field to obtain a chip picture and then machine decoding is carried out on the picture utilizing graph identification software.

When being applied, for example, in a liquid phase biochemical analysis and detection system, the magnetic microchip moves to a designated position in a container through application of a magnetic field and is fixed at this position by a magnetic force, and liquor relieving, liquor changing, washing and other operations can be carried out without leading loss of the magnetic microchip. When the applied magnetic field is withdrawn, the cured ferrofluids having paramagnetism in the magnetic microchip loss magnetism and have no mutual attraction to difficulty generate aggregation, and the magnetic microchips can be dispersed and resuspend in the liquid phase system through low-strength mechanical oscillation or agitation.

Preferably, the magnetic microchip does not generate interference or pollution in samples derived from various sources through adoption of a bioinert transparent encapsulating material, and various biomolecules (capture substances) are immobilized on its surface through a coupling chemical method known in the art so as to react with a specific target molecule (target substance) and a molecular marker in the sample, so that a physical signal that can be detected is generated on the surface of the magnetic microchip to achieve an objective of detection. Thus, in some embodiments, ligand molecules including but not limited to protein, an antibody, a polypeptide, nucleic acid, small molecules, organic compounds, inorganic compounds and the like are coupled with the surface of the magnetic microchip for capturing analytes in the sample.

Preferably, modification methods known in the art can also be utilized to couple some hydrophilic polymers such as PEG; glucan, chitosan and alginate to the surface of the magnetic microchip to provide richer coupling sites, inhibit specific adsorption and improve hydraulic performance of the magnetic microchip.

Another aspect of embodiments of the present application also provides use of the magnetic microchip having a graph code, for example use in the fields of biology, chemistry, biochemical analysis and detection.

For example, embodiments of the present application provide a substance analyzing method, comprising:

providing the magnetic microchip having a graph code;

connecting at least one capture substance on the magnetic microchip, the capture substance being capable of specifically capturing a corresponding target substance;

dispersing the magnetic microchips in a liquid phase system possibly containing the target substances, and keeping the magnetic microchips to be in a suspension state;

sufficiently capturing the target substances possibly existing in the liquid phase system by the capture substances;

taking the magnetic microchips out of the liquid phase system through action of a magnetic field, and imaging in an optical channel having a set wavelength to determine whether the magnetic microchips have capture substances or not and/or quantitatively analyze the concentrations of the target substances in the liquid phase system.

In some embodiments, the substance analyzing method comprises: keeping the magnetic microchip to be in a suspension state in the liquid phase system at least through a mechanical agitation manner or action of an alternating magnetic field.

Further, the liquid phase system may also contain labeling substances for indicating whether the capture substances react with the target substances or not. Preferably, the capture substances and/or the target substances are modified with the labeling substances.

Further, the optical channel having a set wavelength is selected from any one or a combination of more than two of a transmission optical channel, a reflection optical channel, a fluorescence channel and a chemical optical channel, but not limited thereto.

The technical solution of the present application will be further described in combination with typical examples below.

The magnetic microchip (also referred to as a superparamagnetic microchip having an optical graph code) having a graph code applicable to the following examples of the present application is flat (length and width are significantly larger than thickness), typical length and width sizes are no more than 100 μm, the thickness is no more than 2 μm, for example, the magnetic microchip can be 25×15×1.5 μm in dimension.

Further, the base material of the magnetic microchip can be silicon dioxide, wherein, opaque microstructures formed by cured ferrofluids are contained at a plurality of preset positions.

Further, the magnetic microchip can be prepared by a CMOS compatible process in a semi-conductor process facility.

Figure 2:
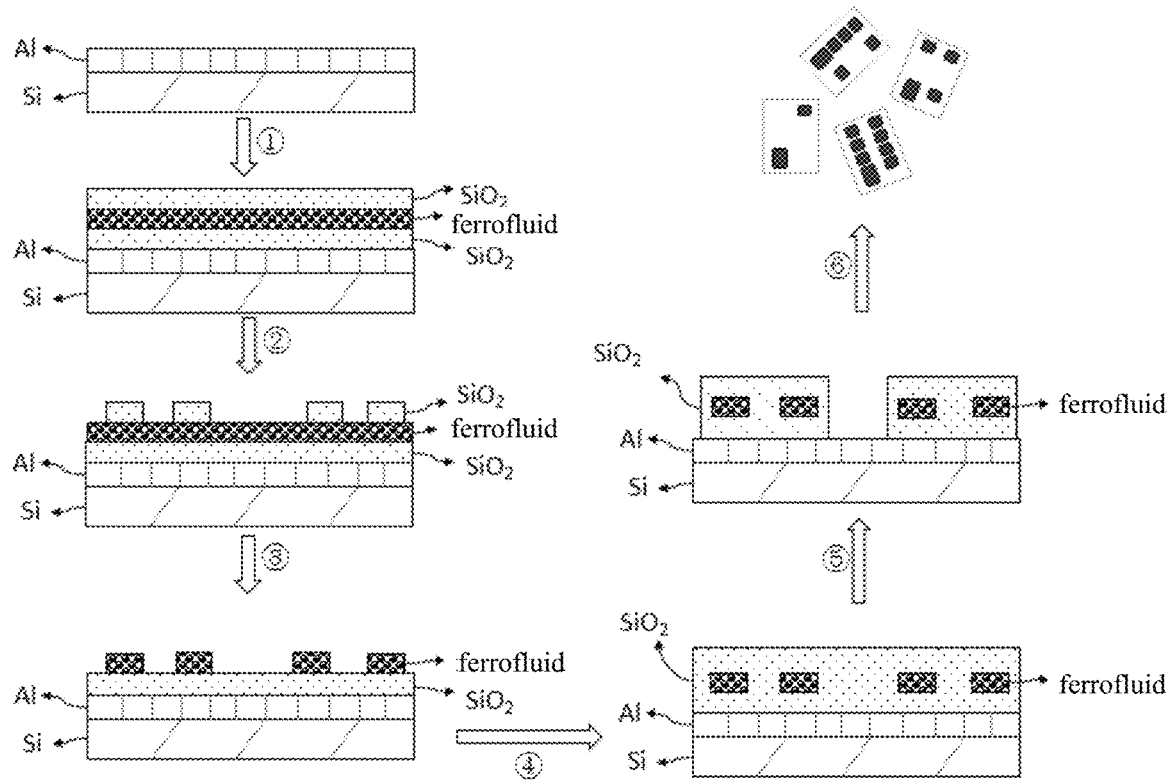
FIG. 2 is a preparation process flow chart of a magnetic microchip having a graph code in one typical embodiment of the present application.

Further, a process for preparing the magnetic microchip is as shown in FIG. 2, which may comprise the following steps: ① a chemical deposition and spinning process in micromachining; ② a photoetching and etching process in micromachining; ③ a chemical deposition process in micromachining; ④ a photoetching and etching process in micromachining; ⑤ a releasing process in micromachining.

More particularly, the preparation process may comprise:

1) forming a thin layer of metallic aluminum as a sacrificial layer on a substrate (for example, Si wafer) commonly used in a semi-conductor process through a metal plating process, wherein the Si wafer can be 4 inch or 6 inch in dimension and undergoes evaporation plating by adopting an electronic beam (e-beam), and the formed metallic aluminum can have a thickness of about 100 nm.

2) depositing a layer of SiO2 as a base layer on the sacrificial layer. For example, SiO2 having a thickness of about 1500 nm can be deposited by adopting a plasma enforcement chemical evaporation deposition (PECVD) manner.

3) uniformly coating a layer of ferrofluid on the base layer through a spin-coating method, and heating to cure the ferrofluid. The ferrofluid can be synthesized through a chemical method known in the art or can directly use a commercialized product. For example, the ferrofluid may include but is not limited to ferrite series ferrofluid (such as $Fe_3O_4$, $\gamma$-$Fe_2O_3$, $MeFe_2O_4$ (Me=Co, Ni, Mn, Zn and other metal elements); metal series ferrofluid (Ni, Co, Fe or other metal microparticles and alloy microparticles thereof); iron nitride series ferrofluid and the like. For example, a ferrofluid consisting of iron oxide nanoparticles dispersed in alkyl naphthalene can be used and coated on the base layer by adopting a centrifugal spinning manner, and the spinning conditions are as follows: a spin coater operates for 15 seconds in 1000 rpm, the formed ferrofluid film has a thickness of about 1.3 μm, and a heating condition is as follows: a hot plate is heated for 15 min at 120° C.

In this step 3), two processes, namely centrifugal spinning and heating, function as removing the base carrying liquid (organic solvent) of the ferrofluid. The former makes the base carrying liquid thrown away out of the surface of the wafer, and the later makes it volatilized. After being cured, magnetic solid nanoparticles form colloidal aggregates, but, the connected surfactant molecule and the adsorbed solvent molecule (base carrying liquid molecule) on the surfaces of the magnetic solid nanoparticles allow the magnetic solid nanoparticles to be still kept in a separation state. And therefore, the superparamagnetism of the cured ferrofluid is retained.

4) depositing a layer of SiO2 as a photoetching protection layer on the cured ferrofluid layer again.

5) spinning resist coating on the surface of the wafer, and transferring a coding graph to the resist coating through a photoetching process (exposing and developing).

6) selecting proper dry etching processes (such as reaction plasma etching/RIE and induction plasma etching/ICP) as to different materials to successively etch away a SiO2 layer (for example, microscopic examination results refer to FIG. 3a-FIG. 3) which is not protected by resist coating and formed in the above step 4) and the cured ferrofluid layer formed in the above step 3) on the wafer, so as to expose the SiO2 layer (for example, microscopic examination results refer to FIG. 4a-FIG. 4b) formed in the above step 2).

7) depositing a layer of SiO2 as an encapsulating layer to completely wrap the cured ferrofluid portion inside the magnetic microchip.

Figures 5A, 5B:
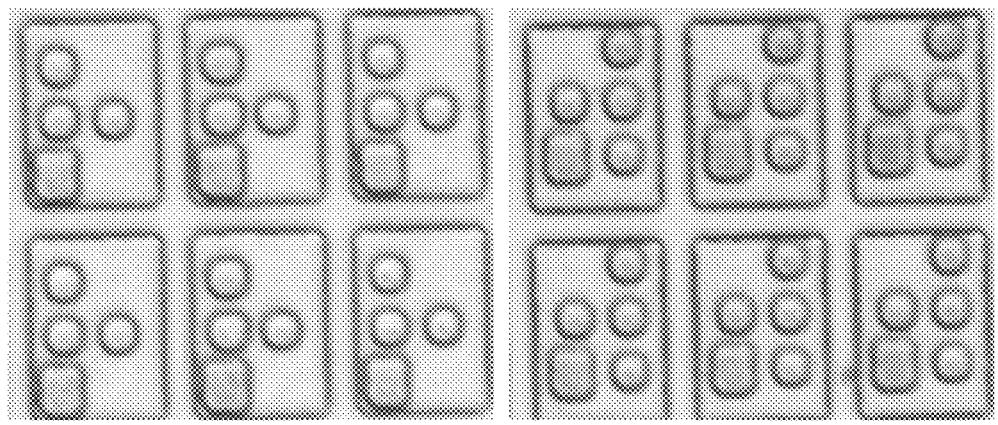
FIG. 5a-FIG. 5b are metallographic microphotographs of two kinds of magnetic microchips having graph codes in one embodiment of the present application, respectively.

8) overlaying using a photoetching process to isolate each magnetic microchip from surrounding other magnetic microchips and expose a Al sacrificial layer (for example, microscopic examination results refer to FIG. 5a-FIG. 5b) formed in the step 1).

Figure 6:
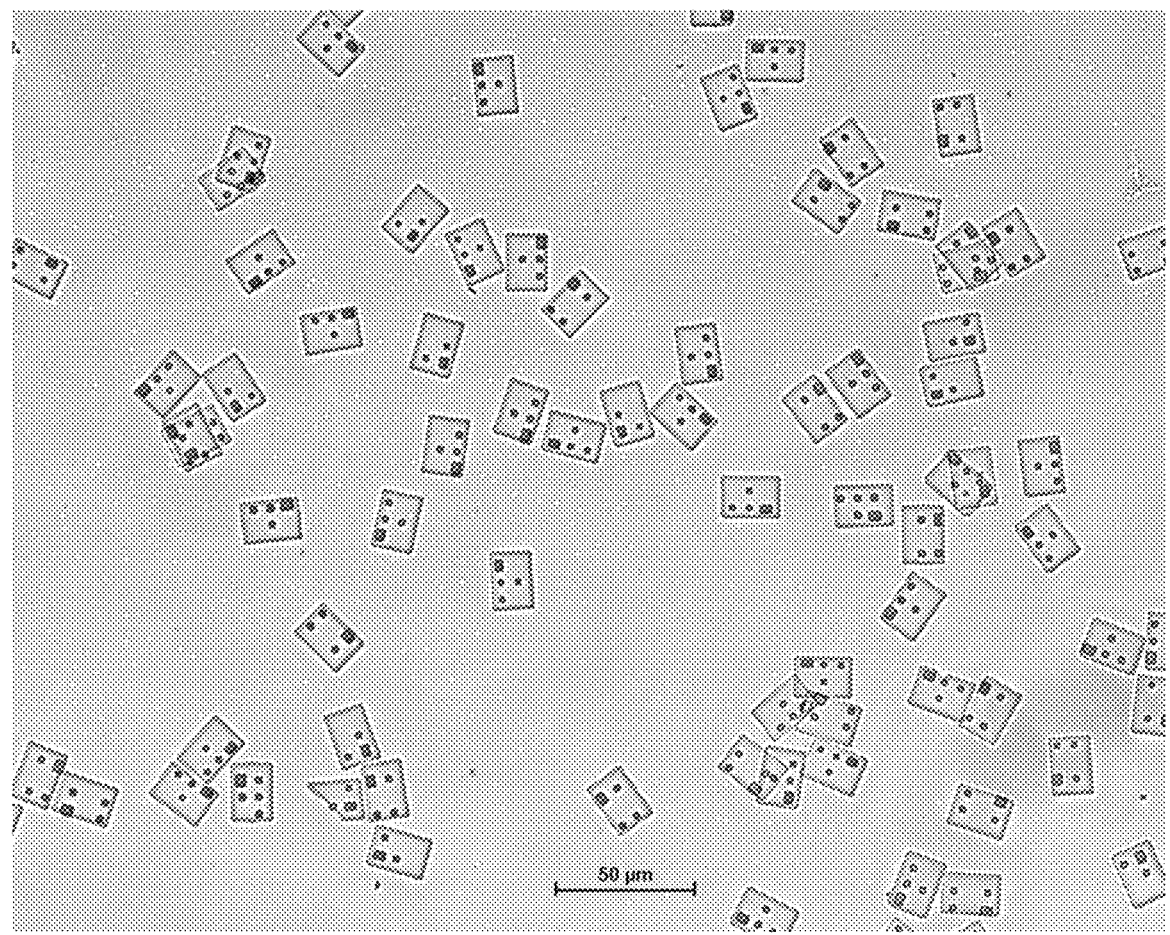
FIG. 6 is an optical microphotograph of the obtained magnetic microchip having a graph code when dispersed in a liquid phase system in one embodiment of the present application.
Figure 7:
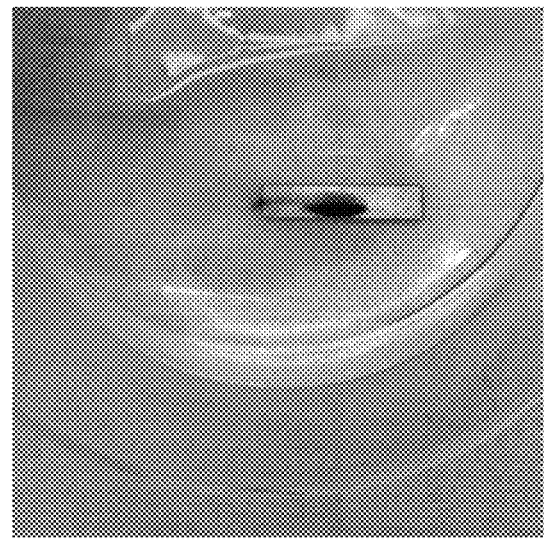
FIG. 7 is a graph of a magnetic microchip having a graph code in a magnetic field in one embodiment of the present application.

9) placing the wafer in a solvent (for example, diluted hydrochloric acid) capable of dissolving the sacrificial layer. After the sacrificial layer is dissolved, the above microchip is dropped from the substrate into a liquid phase (for example, microscopic examination results refer to FIG. 6). Due to superparamagnetism, the magnetic microchip can be separated from a suspension state through an applied magnetic field (for example, referring to FIG. 7) so as to perform washing or other treatments on the magnetic microchip.

Further, ligands (such as a nucleic acid probe and an antibody) for different target molecules are coupled to the SiO2 surface of the above magnetic microchip according to application demand, so as to obtain the magnetic microchip for multiplex assay.

Obviously, the above magnetic microchip is simple and economic in preparation process, is stable and prone to identifying in code structure, and is beneficial for multiplex assay application. In addition, the washing and separation manner of the magnetic microchip is simple, and is beneficial for achievement of automation of a detection process.

Moreover, since the above magnetic microchip contains the cured ferrofluid, several physical properties of the ferrofluid are utilized, that is, ① the ferrofluid is a colloid suspension of a large amount of superparamagnetic nanoparticles, and can be intensely magnetized by an external magnetic field. And after the external magnetic field is withdrawn, magnetization is lost. Thus, a magnet can be used to attract the magnetic microchip in the liquid phase system so that the magnetic microchip is separated from the suspension. When no external magnetic field exists, the magnetic microchip can freely suspend in the liquid phase system again. ② A material (for example, ferriferous oxide) consisting of the ferrofluid is opaque, and a plane graph code similar to a two-dimensional bar code can be constituted by arranging a plurality of the cured ferrofluid in the transparent magnetic microchip according to specific positions. Different types or uses of magnetic microchips are coded by changing the arrangement manner of the cured ferrofluid in the magnetic microchip.

Further, a suspension array can be formed by utilizing a plurality of magnetic microchips having different graph codes, and is applied to parallel detection (that is, multiplex assay) of a plurality of molecules such as nucleic acids, proteins and antigens in a liquid sample, and the suspension array can be conveniently separated through the applied magnetic field without a complicated separation device.

The above magnetic microchip can be applied to quantitative detection analysis on biomolecules (including but not limited to an antigen, nucleic acid, a protein, a polypeptide, polysaccharide and the like), for example, immunoassay application based on an antibody affinity reaction and molecular diagnostics application based on nucleic acid hybridization reaction.

For example, since in the above magnetic microchip, SiO2 is adopted to form a transparent material substrate, it is easily conceived for those skilled in the art that a commonly used solution is adopted to directly connect a biological probe molecule on the coding suspension microchip, the procedure is simpler, and this biological probe molecule can be selected from a protein, a polypeptide, DNA, RNA, LNA, PNA and the like, but is not limited thereto.

Further, in order to facilitate detection, it is possibly needed to modify a fluorescence label, a radiolabel or other specific labels on the biological probe molecule, alternatively, the above specific labels and the like are added in the subsequent liquid phase reaction system. Of course, these solutions can be selectively adopted according to practical application demand.

A general process of detecting various determined molecules utilizing the above magnetic microchip is as follows:

First, mixed means such as agitation, vibration and an alternating magnetic field are utilized to keep sufficient amounts of magnetic suspension microchips to suspend in a sample liquid to react for a certain time, in this process, probe molecules modified on the surfaces of the magnetic microchips will capture corresponding target molecules;

then, the magnetic microchips are separated from the sample solution by virtue of centrifuging and other means, and are washed;

later, the sedimentary microchips are imaged in selected optical channels.

For example, optical imaging is performed on the above magnetic microchips by adopting a visible light channel and a fluorescence channel. Where, a code of each chip can be read in the visible light channel to determine an identity of the target molecule captured by this chip; and quantitative analysis is performed on the concentration of the target molecule in the fluorescence channel. In combination with results of a plurality of different microchips, detection on a plurality of determines in the sample can be simultaneously achieved.

More particularly, a plurality of nucleic acid amplification products (nucleic acid detection) in a biological sample are detected by utilizing the above magnetic microchip.

Amplification of a plurality of template molecules in the same sample can be conveniently achieved by utilizing the magnetic microchip in combination with a conventional polymer chain reaction (PCR) technology. Since different amplification products are distinguished without using a plurality of fluorescence channels, this application avoids restriction on the number (only 4 in general) of the existing multiplex PCR instrument fluorescence channels, and can greatly improve the throughput of PCR; meanwhile, a plurality of probes connected with different fluorophores are not needed to be specifically designed and synthesized, and an expensive multi-channel real-time quantitative PCR instrument is not needed to be used either, thereby greatly reducing use cost.

Implementation Steps:

First, the quantity of different templates to be detected is determined according to application demand. The quantity is generally about 4~20 (which is not limited thereto, and is increased and reduced by those skilled in the art according to actual situations).

Magnetic microchips having different codes are prepared, each code corresponds to one to-be-detected template nucleic acid. Particular operations are well known in the art.

For the magnetic microchip having each code, a PCR primer (or a probe) of to-be-detected template nucleic acid is covalently immobilized on the surface of the magnetic microchip by utilizing a chemical modification method known in the art. For example, after the silicon dioxide surface of the magnetic microchip is washed using piranha solution, the magnetic microchip reacts with an ethanol solution of amino silane so that the surface of the magnetic microchip undergoes amination, the magnetic microchip is washed and then reacts with a glutaraldehyde aqueous solution so that the surface of the magnetic microchip undergoes hydroformylation, and finally, the magnetic microchip reacts with a terminal amino modified primer so that the primer is connected to the surface of the chip.

Before detection, first, the magnetic microchips having different codes and containing the above modification PCR primers are mixed together in equal amount. Later, the chip mixed liquid and other reagents (including dNTP, polymerase, ligase and fluorochrome) required by PCR reaction constitute a PCR mixed liquid in an appropriate proportion (determined by specific PCR reaction, which is well known by those skilled in the art). PCR reaction is carried out after a sample is added. Where, a usable sample includes but is not limited to solution, cell extractive, whole blood, serum, urine, saliva and forensic medicine specimen.

Specific PCR reaction forms can b selected according to actual situations. For example, bridge PCR most commonly used in a solid phase PCR technology can be adopted, that is, two primers required by each PCR reaction are simultaneously immobilized on the surfaces of the magnetic microchips having corresponding codes. A result of an amplification reaction is that a large number of hybridized double chains are formed on the magnetic microchips, and conventional micromolecule fluorochromes such as SYBR are combined on these double chains to generate signals.

Also for example, isothermal amplification is also carried out, in such a way, requirements on the PCR instrument can be further reduced. In particular, a rolling circle amplification (RCA) technology known in the art can be used. First, a capture probe of a to-be-detected molecule is immobilized on the surface of the magnetic microchip. After being captured through complementary hybridization reaction, the to-be-detected molecule and an adaptor in reaction liquor are connected into a chain under the action of ligase. A sequence of a primer contained in the adaptor initiates RCA reaction, and finally, a large number of fluorescence probes are caused to be hybridized on the amplification product molecules to generate signals.

After PCR reaction is ended, solid-liquid separation is carried out on the reaction system utilizing a magnet to remain the magnetic microchip, the microchip is repeatedly washed, and finally suspends in buffer solution. A proper quantity of chips are taken from this suspension to respectively collect images of the chips under visible light and fluorescence channels by utilizing an imaging apparatus, so as to obtain an identity of each chip (namely the identity of the detected molecule) and corresponding fluorescence intensity (namely the concentration of the to-be-to detected molecule can be calculated by using standard curves drawn by simultaneously reacting series standard substances whose concentrations have been known).

More particularly, non-labeling multiplex assay (nucleic acid detection) is also carried out utilizing the above magnetic microchip in combination with a molecular beacon probe. For non-labeling detection without using amplification reaction, a molecular beacon known in the art can be used as a probe. Its characteristic lies in that a detection signal can be triggered directly through a combination event of an objective and the probe, without adding another indicator.

Implementation Steps:

A probe is determined according to specific situation of to-be-detected nucleic acid in a sample. The sample useful in the present application includes but is not limited to solution, cell extractive, whole blood, serum, saliva and forensic medicine specimen. As to sequences of various to-be-detected nucleic acids, specific molecular beacons are designed.

The surfaces of the above magnetic microchips are modified with corresponding probes. The specific process is described as above. When in detection, a sample is added in buffer solution of a corresponding magnetic microchip to be mixed and react. For a microchip modified with a probe, such as a molecular beacon, as long as it combines with a target molecule, due to a working principle of the molecular beacon known in the art, its second-level structure will change to lead separation of fluorophores and cancellation aggregates so as to generate a fluorescence signal on the surface of the chip. On the contrary, if the molecular beacon is not combined with the target molecule, and its conformation keeps unchanged, the signal is not generated.

After the reaction is ended, each magnetic microchip is identified through steps similar to washing/imaging steps described as above and its fluorescence signal is obtained, so as to complete detection on contents of a plurality of to-be-detected nucleic acids.

Particularly, the present application is especially suitable for biological analysis application with a standard microwell plate (microplates 6, 12, 24, 48, 96, 384, 1536 wells) as a sample carrier, and achieves parallel detection on a plurality of to-be-analyzed indexes in a large number of samples. For example, a plurality of antigen proteins and the like in a clinic sample are detected utilizing the above magnetic microchip (immunoassay), for example, routine Hepatitis B five-index detection. Such a detection is carried out in a multi-well plate. The implementation steps are as follows:

The quantity of different templates to be detected is determined according to application demand. The quantity is generally about 4~20 (which is not limited thereto, and is increased and reduced by those skilled in the art according to actual demand).

Magnetic microchips having different codes are prepared, and each code corresponds to one to-be-detected protein.

A detection method adopts a conventional sandwich form. First, the surface of the magnetic microchip having each code is activated, for example, the magnetic microchip undergoes amination using amino silane (the method is described as above). A specific antibody (primary antibody) of the to-be-detected protein is covalently immobilized on the activated surface. Subsequently, a certain protein (such as BSA) is also used according to demand so as to block the exposed part of the surface of the chip to reduce non-specific adsorption.

Figure 8:
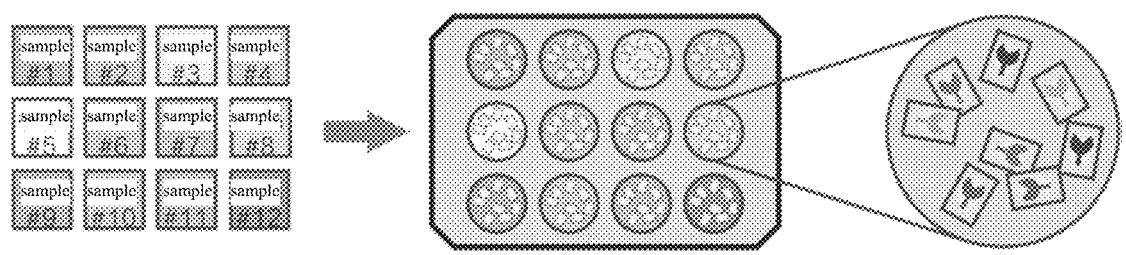
FIG. 8 is a diagram illustrating multiplex assay on a plurality of samples in a microwell plate is performed utilizing a magnetic microchip having a graph code in one typical embodiment of the present application.

The sample useful in the above detection method includes but is not limited to solution, cell extractive, whole blood, serum, urine, saliva and forensic medicine specimen. Referring to FIG. 8, when in detection, different samples and magnetic microchips corresponding to various to-be-detected proteins are mixed in different wells of a multi-well plate, and incubated under an appropriate temperature and vibration condition (or an alternating magnetic field). In such a process, primary antibodies on the surfaces of the magnetic microchips are specifically combined with target proteins in the solution. After incubation is ended, another target-specific antibody (secondary antibody) with a fluorescence label can also be added, and the antigen molecules on the surfaces of the previously captured magnetic microchips carry fluorescence (but the signal of the present method is not limited thereto, and a chemical light-emitting signal and the like are also used as needed) through antigen-antibody reaction. Finally, a signal of each to-be-to detected antigen is obtained through the above imaging steps, thereby completing quantitative detection.

Due to universality of immunoassay, the to-be-detected substance is not limited to antigen protein, and may also include various substances having specific antibodies, for example drug molecules, metabolin molecules, pathogens and cells, which are well known by those skilled in the art.

Example 1: Surface Modification and Functionalization of a Magnetic Microchip

1) A proper amount (for example, 500,000-5,000,000 pieces, determined according to specific demand, and graph codes on various magnetic microchips can also be regulated according to actual application demand) of magnetic microchips prepared by a process as shown in FIG. 2 is taken to be placed in 1.5 mL microcentrifuge tube.

2) Washing is carried out twice using 95V/V % ethanol. After each washing, the chips are enriched to the bottom of the centrifuge tube with a strong magnet or a magnetic gate special for the microcentrifuge tube, and then supernatant is removed using a pipettor.

3) 1000 μl of 5 wt % amino silane APDMS (prepared using 95% ethanol) is added, sufficient vibration is carried out, ultrasound is carried out for a while, and then the microcentrifuge tube is placed on a vortex oscillator to shake for 30 min.

4) Washing is carried out three times using absolute ethyl alcohol according to the method in the step 2).

5) Washing is carried out once using N,N-dimethylformamide (DMF) to remove supernate.

6) In a fuming cupboard, 10 wt % succinic anhydride solution (a solvent: DMF) is added to the tube to react for 6 hours under the protection of $N_2$.

7) Washing is carried out three times using deionized water to remove supernate.

8) Washing is carried out once using 0.1M MES buffer solution precooled at 2-8° C.

9) 400 μl of 50 mM NHS buffer solution and 400 μl of 100 mM EDC buffer solution which are freshly prepared are added, (a precooling solvent 0.1M MES, pH4.7), sufficient vibration is carried out to shake for 30 min at room temperature.

10) Washing is carried out twice using 1× buffer solution (pH7.2).

11) A to-be-coupled probe (for example, antibody, nucleic acid, etc.) is added, inoculation is carried out for 6 h at room temperature, or shaking is carried out over night at 4° C.

12) Washing is carried out twice using PBST (pH=7.4, which contains 0.2% Tween-20 and prepared by PBS solution) to remove supernate.

13) Washing is carried out once using 1M NaCl solution to remove supernate, and then the remained substance is added into 1000 μl of 1M NaCl solution to carry out shaking reaction for 30 min.

14) Superate is removed by virtue of magnetic adsorption, and inoculation is carried out for 1 hour in 1% BSA (prepared by 1×PBS solution) for blocking.

15) Washing is carried out twice using 1% BSA in 1×PBS to remove supernate, and the remained substance resuspends in a proper solution and stored at 2~8° C.

Example 2 multiplex assay on a nucleic acid marker: high risk human papillomavirus (HPV) is taken as an example.

Human papillomavirus (HPV) belongs to papilloma virus of papovaviridae. At present, the known HPV has more than 200 subtypes, and is divided into 5 viruses (alpha, beta, gamma, mu and nu) and 33 species according to similarity of its genomes. Alpha HPV mainly infects epithelial cells, and more than ten types of HPVs among Alpha HPVs are associated with generation of cancer, and called high risk HPVs. All of HPV typing methods for clinic are based on detection of HPV nucleic acid in a clinical sample. HPV typing detection has an important instructive significance in the aspects of early screening and postoperation follow-up of cervical cancer, cytological detection result shunting, discovery of high risk people, instruction of research and use of HPV vaccines and the like. At present, the commonly used HPV typing detection methods such as membrane reverse hybridization and microarray hybridization are limited in detection throughput and flexibility and bad in data quality and repeatability, also have disadvantages of slow hybridization reaction speed, complicated procedure, time and labor consumption, high hybridization condition dependency degree and the like, and are inconvenient for clinical detection.

A multiplex assay method provided by this example can completely overcome the above deficiencies of the existing technology. The multiplex assay method comprises the following steps that:

1) Multiplex amplification is carried out on 5 high risk HPV gene segments (five types of HPV common in China are selected, such as HPV16,18,31,33,58) in a to-be-detected sample (HPV plasmid 0.1 ng/μL and 2 ng/μL placenta genome DNA, tissues containing HPV nucleic acid are stimulated to extract total DNA) utilizing a multiplex PCR method, and a biotin label is introduced into one end (for example 5'end) of a nucleic acid molecule of the amplification product through a modification primer. Meanwhile, as a positive control, a gene of a human globin subunit beta (HBB) is also amplified.

2) 10 μL of PCR product and 40 μL of hybridization liquid (5×SSC, 0.05% Tween® 20) containing 6 coding magnetic microchips (each is about 200 pieces, respectively carrying a hybridization probe for one HPV amplification product and a hybridization probe for HBB, and prepared by reference to the solution in example 1) are respectively taken and mixed, and then the obtained mixture is incubated for 30 min by virtue of vibration at 55° C. under the vortex oscillating condition of 700 rpm. In this step, amplification products are each captured by corresponding probes on the surfaces of the magnetic microchips. Where, a DNA sequence (5' to 3') of the capture probe coupled to each chip is shown in Table as below.

| | | | |
|---|---|---|---|
| HPV16 | SEQ ID NO 1 | AAAAAAAAAAAAATCTCACCTCCCACCTCT GTCATTATGTGCTGCCATATCTACTTCAGA |
| HPV18 | SEQ ID NO 2 | AAAAAAAAAAAAATCTCACCTCCCACCTCT ATATGTGCTTCTACACAGTCTCCTGTACCT |
| HPV31 | SEQ ID NO 3 | AAAAAAAAAAAAATCTCACCTCCCACCTCT CAATATGTCTGTTTGTGCTGCAATTGCAAA |
| HPV33 | SEQ ID NO 4 | AAAAAAAAAAAAATCTCACCTCCCACCTCT TGACTTTATGCACACAAGTAACTAGTGACA |
| HPV58 | SEQ ID NO 5 | AAAAAAAAAAAAATCTCACCTCCCACCTCT AAATATGTCTGTGTGTTCTGCTGTGTCTTC |
| HBB | SEQ ID NO 6 | AAAAAAAAAAAAATCTCACCTCCCACCTCT GACATTATGCACTGAAGTAACTAAGGAAGG |

3) Chips are separated by virtue of magnetic adsorption, and washed with 100 μL of washing liquid (1×SSC/0.01% A Tween® 20).

4) 0.2 μg/ml phycoerythrin (a common fluorescin)-conjugated streptavidin (streptavidin-conjugated R-phycoerythrin, SAPE) is added to dye the chips. In this process, SAPE is combined with biotin molecules carried by amplification product nucleic acids captured to the chips so that the surfaces of the chips have fluorescence. After being dyed, the chips are washed and resuspend in the washing liquid.

5) 50 μL of each sample is transferred to a 384-well plate with a transparent bottom. The well plate is placed on a microwell plate imager (plate imager, for example, Cytation 3 multifunctional microwell plate detector from BioTek company), 100× enlarged image (including a light field image and a PE channel fluorescence images) of each sample well is photographed under fixed exposure conditions. Image identification, decoding and fluorescence signal extraction are carried out on the chips in the images, and concentrations of HPVs in the samples can be obtained through a statistical analysis method in combination with a standard curve.

Typical experiment results are as follows:

(1) HPV typing specificity. As shown in Table below, one HPV plasmid (totally 5) and placenta genome DNA are respectively added into a mixed system containing 6 chips, and under each condition, only a coding chip corresponding to the added HPV and an HBB chip (positive control) exhibit high fluorescence signals.

| | HBB | Probe 16 | Probe 18 | Probe 31 | Probe 33 | Probe 35 | Probe 39 |
|---|---|---|---|---|---|---|---|
| ddH₂O | 211 | 206 | 140 | 99 | 178 | 134 | 132 |
| gDNA | 6407 | 112 | 111 | 86 | 118 | 146 | 147 |
| HPV16 | 106 | 5936 | 111 | 115 | 64 | 131 | 160 |
| HPV18 | 290 | 267 | 8353 | 106 | 163 | 164 | 65 |
| HPV31 | 353 | 172 | 165 | 7867 | 265 | 97 | 167 |
| HPV33 | 297 | 9 | 48 | 170 | 8863 | 209 | 80 |
| HPV35 | 118 | 79 | 84 | 109 | 257 | 5027 | 140 |
| HPV39 | 211 | 105 | 285 | 123 | 398 | 197 | 4097 |

Figure 9:
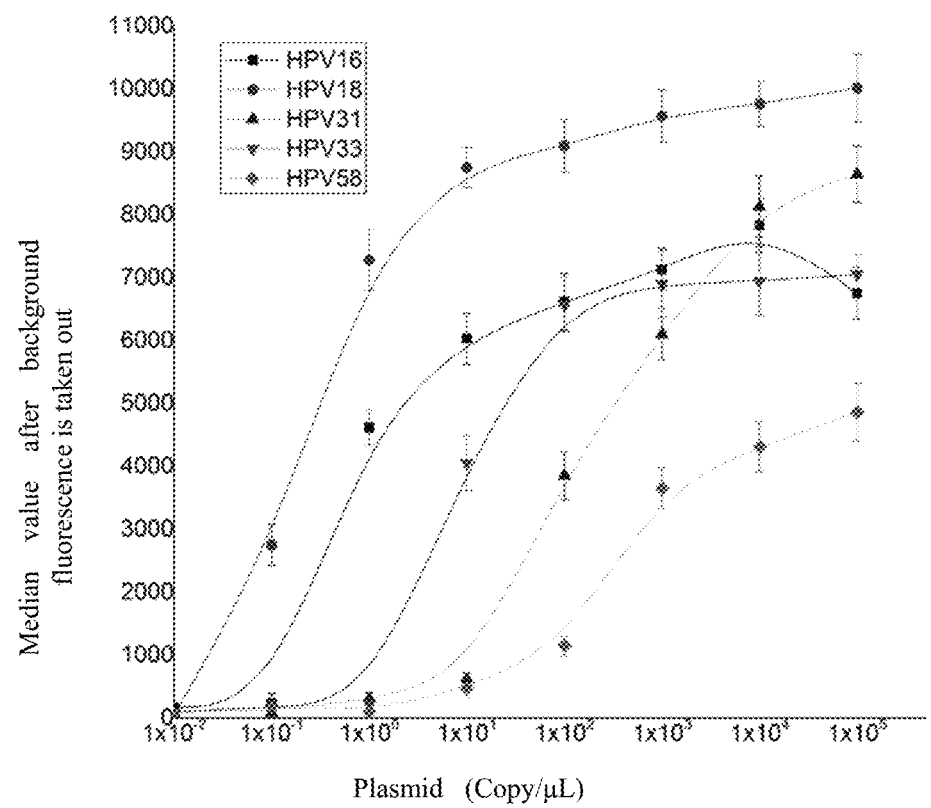
FIG. 9 is a sensitivity representation graph illustrating HPV detection is performed utilizing a magnetic microchip in example 2 of the present application.

(2) HPV detection sensitivity. As shown in FIG. 9, the sensitivity on HPV16 is up to 1 copy/μL, the sensitivity on HPV18 is 0.1 copy/μL, and the sensitivities on HPV31, 33, 58 are up to 10 copies/μL.

Example 3 immune sandwich method multiplex assay on cytokines: human TNF, IL-1β, IFNγ and FGF-19 in human serum are taken as examples.

A detection method in this example comprises the following steps that:

1) 4 coding magnetic microchips (prepared by reference to the solution in example 1) which have been respectively coupled with an anti-human TNFα antibody, an anti-human IL-1β antibody, an anti-human IFNγ antibody and an anti-human FGF-19 antibody constitute a mixed suspension.

100 μL of chip suspension and 100 μL of sample (or a standard substance, with a concentration ranging from 0.5 pg/ml to 10 ng/ml) are added into one well of a 96-well plate.

2) The 96-well plate is placed on a vortex mixer for vibration reaction at the speed of 700 rpm. Reaction time can be shortened to 1 hour (at room temperature) according to specific requirement or overnight (4° C.). In this step, to-be-detected cytokines are each captured by the surface antibodies of corresponding magnetic microchips.

3) The 96-well plate is placed on a plate washer equipped with a magnetic fitting (such as 405 LS type plate washer from BioTek company), the microchips are firmly adsorbed at the bottom of the well plate by utilizing the magnetic fitting, and washed (circulating three times, the amount of the washing liquid is 250 μl each time) with the washing liquid being 1×PBST.

4) 100 μl/well of detection antibodies carrying biotin labels are added and react on the vortex mixer for 1-2 hours. In this step, the detection antibodies are combined to the corresponding cytokines that have been captured to the surfaces of the chips.

5) Washing is carried out with the magnetic plate washer (similar to the above step 4).

6) 100 μl/well of 0.5 μg/ml SAPE is added to dye the chips.

7) Washing is carried out with the magnetic plate washer (similar to the above step 4).

Figure 10:
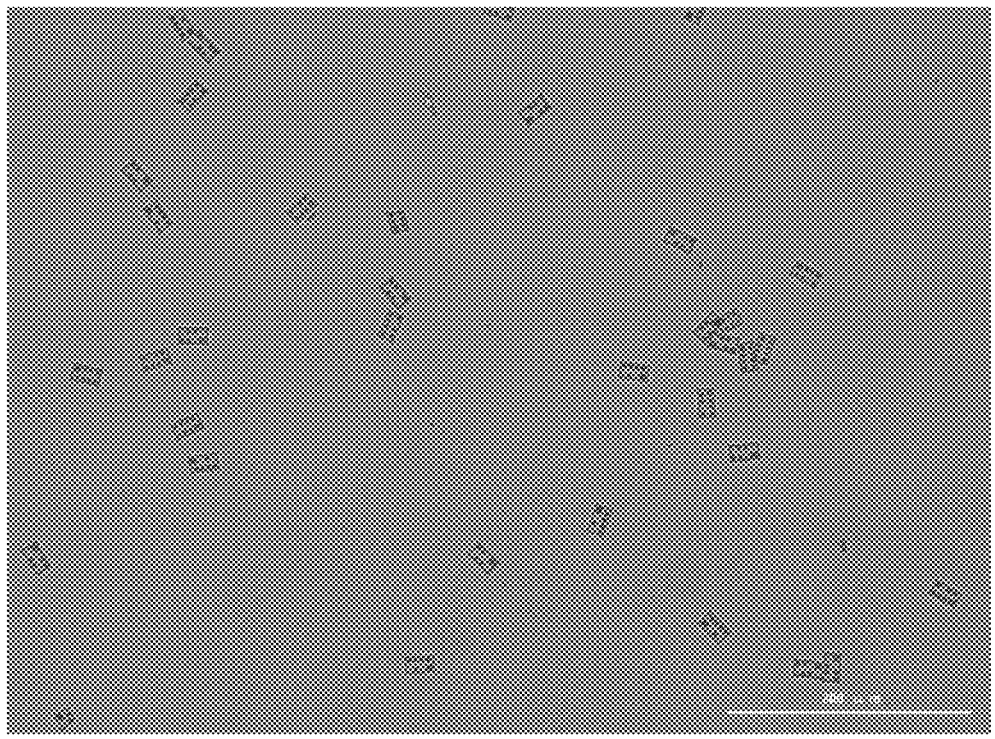
FIG. 10 is a light field image of a detection system containing a magnetic microchip in example 3 of the present application.
Figure 11:
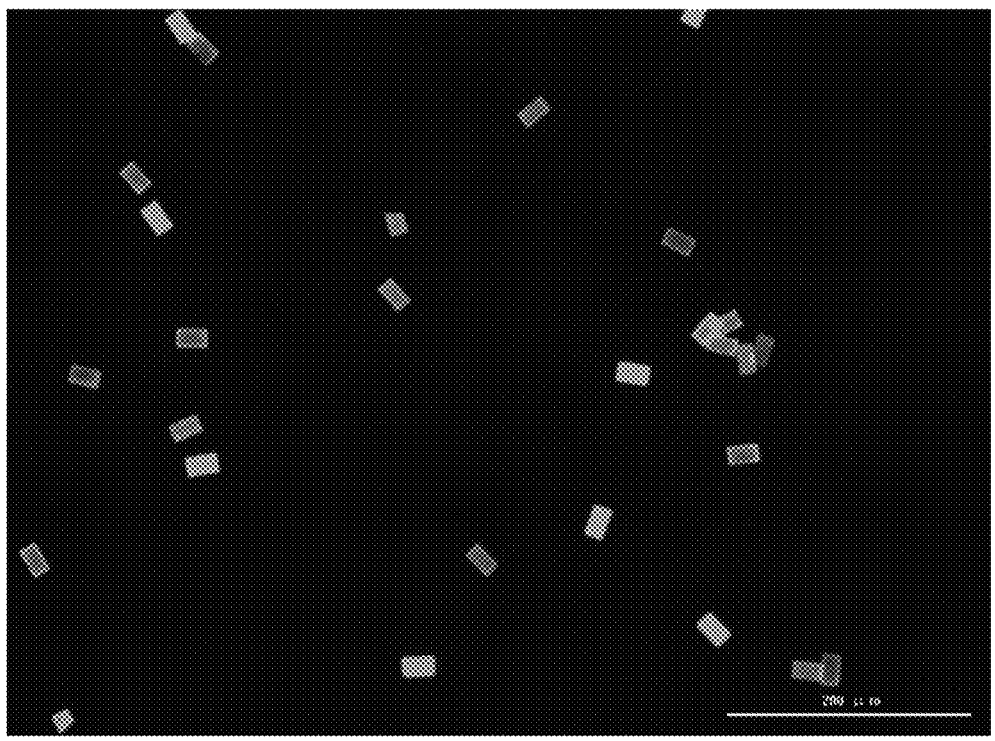
FIG. 11 is a fluorescence image of a detection system containing a magnetic microchip in example 3 of the present application.

8) The chips are placed on a microwell plate imager (plate imager, for example, Cytation 3 multifunctional microwell plate detector from BioTek company), 100× enlarged images (including a light field image and a PE channel fluorescence image, as shown in FIG. 10 and FIG. 11 respectively) of each sample well is photographed under fixed exposure conditions. Image identification, decoding and fluorescence signal extraction are carried out on the chips in the images, and a concentration of each to-be-detected protein in the sample is obtained through a statistical analysis method in combination with a standard curve.

Figure 12:
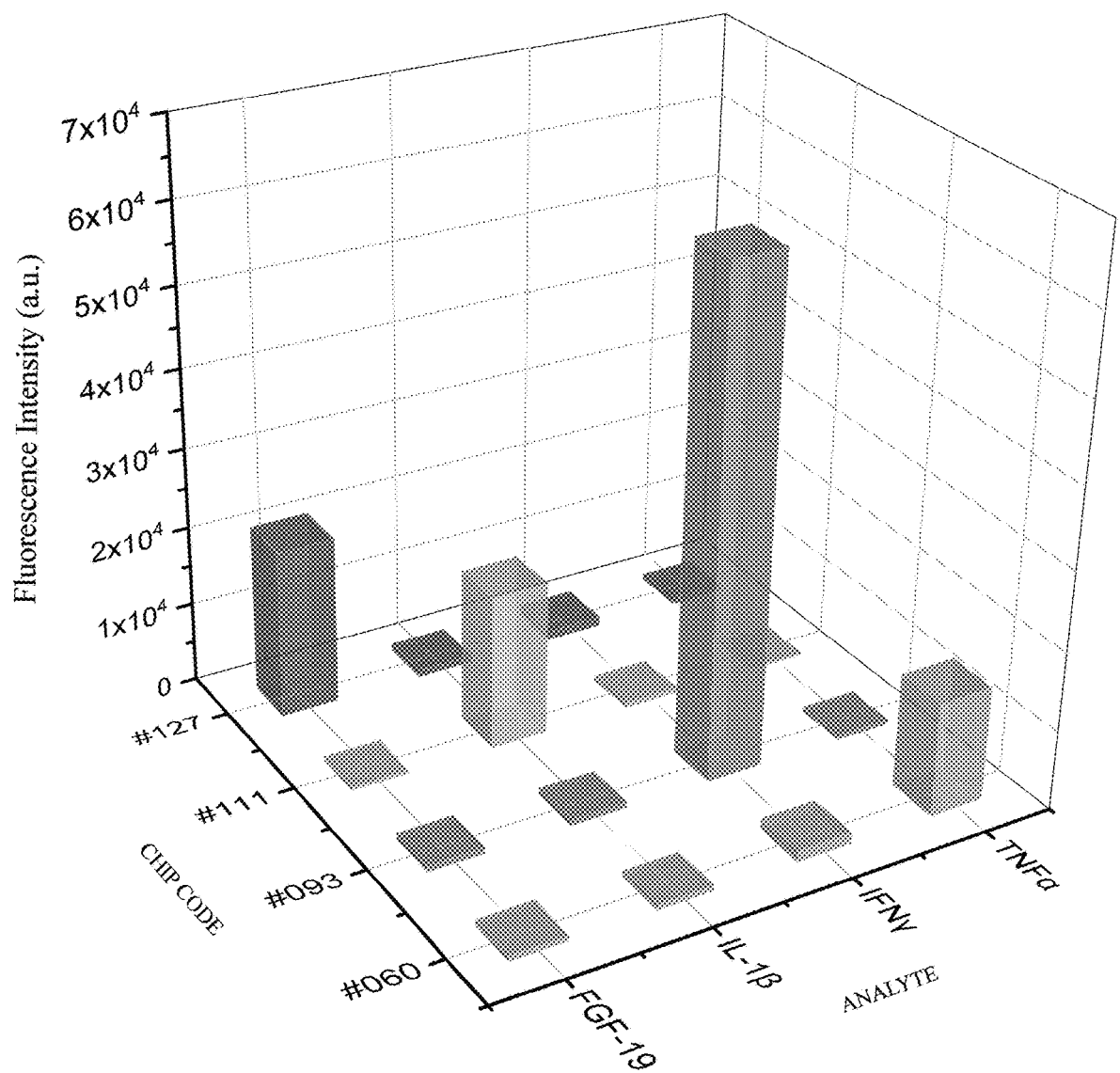
FIG. 12 is a specificity representation graph illustrating multiplex assay is performed utilizing a magnetic microchip in example 3 of the present application.

Typical experiment results are as follows:

(1) Detection specificity: refer to FIG. 12, illustrating signal response situations of various chips when 4 chip mixed liquids (wherein, code #060 chip detects TNFα, #093 detects human IFNγ, #111 detects IL-1β, and #127 detects human FGF-19) are respectively added with 1 cytokine. It can be seen that non-specific interference signals on the chips are in an extremely low level.

Figure 13:
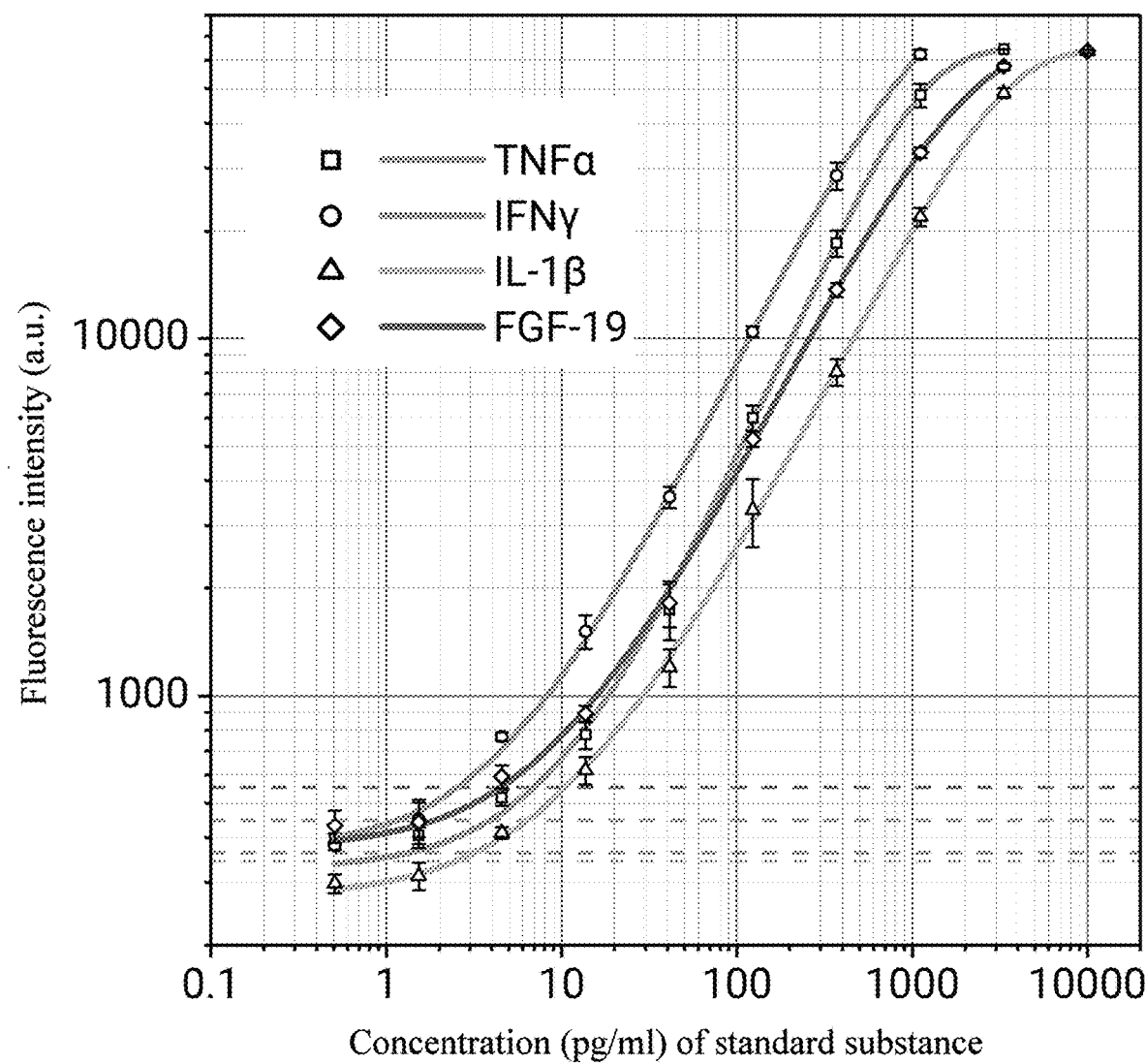
FIG. 13 is a multiplex assay sensitivity representation graph illustrating detection is performed utilizing a magnetic microchip in example 3 of the present application.

(2) Multiplex assay sensitivity: refer to FIG. 13, illustrating a standard curve established by 4 cytokine standard substance detection values (standard samples having the same concentration are mixed). The lowest detection limits (as shown in imaginary lines) are respectively 2.7 (TNFα), 0.5 (IFNγ), 2.1 (IL-1β), and 4.0 pg/ml (FGF-19).

Figure 14:
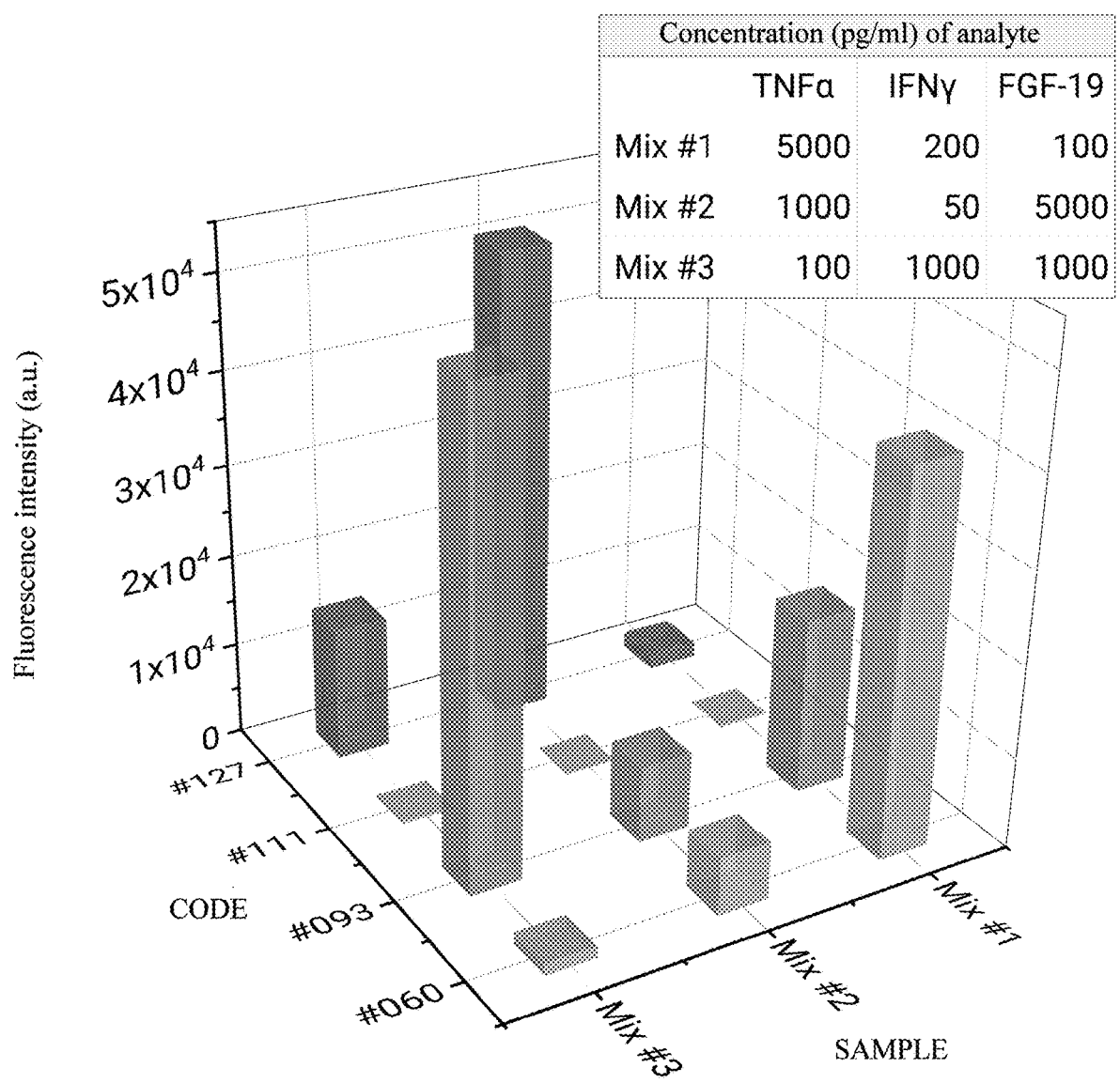
FIG. 14 is a signal response representation graph illustrating multiplex assay is performed utilizing a magnetic microchip in example 3 of the present application.

(3) Multiplex assay: refer to FIG. 14, illustrating signal responses of 3 test samples consisting of different concentrations of TNFα, IFNγ and IL-1β. It can be seen that a signal level is highly consistent with a content level of a corresponding analyte.

It should be understood that the above embodiments only illustrate the technical conception and features of the present application for the purpose of allowing persons familiar to this technology to know the content of the present application and implement the present application, and whereby cannot limit the protection scope of the present application. Equivalent variations or modifications made according to the spirit of the present application all fall within the protection scope of the present application.

What is claimed is:

1. A preparation method of a magnetic microchip having a graph code, comprising:
providing a transparent substrate layer;
applying a film formed by ferrofluid on the transparent substrate layer;
at least removing a portion of base carrying liquid in the film so that at least a portion of the film is cured to form a ferrofluid layer;
machining the ferrofluid layer to form an opaque microstructure as the graph code;
wrapping the opaque microstructure with a transparent material to form the magnetic microchip.

2. The preparation method according to claim 1, wherein:
the step of applying the film formed by the ferrofluid comprises coating the ferrofluid on the transparent substrate layer to form the film;
the step of forming the ferrofluid layer comprises heating to remove at least a portion of base carrying liquid in the film, thereby forming the ferrofluid layer.

3. The preparation method according to claim 1, wherein, the ferrofluid comprises magnetic solid particles, a surfactant and a base carrying liquid, the base carrying liquid being sufficient to cooperate with the surfactant to disperse the magnetic solid particles to form a colloid suspension; the magnetic solid particles have a particle size of 1 nm~1000 nm; the ferrofluid comprises any one or a combination of more than two of ferrite series ferrofluid, metal series ferrofluid and ferric oxide series ferrofluid; the material of the ferrite series ferrofluid comprises any one or a combination of more than two of $Fe_3O_4$, $\gamma\text{-}Fe_2O_3$ and $MeFe_2O_4$, wherein, Me is at least selected from Co, Ni, Mn or Zn; the metal series ferrofluid comprises metal microparticles formed by any one or a combination of more than two of Ni, Co and Fe.

4. The preparation method according to claim 3, wherein, in the ferrofluid layer, adjacent magnetic solid particles are isolated at least by an organic molecule and/or an inorganic molecule derived from the ferrofluid; the organic molecule and/or the inorganic molecule comprises a surfactant molecule and/or a base carrying liquid molecule derived from the ferrofluid; the ferrofluid layer contains 50V/V %~99V/V % of magnetic solid particles, 0.5V/V %~50V/V % of surfactant molecule and 0.5V/V %~50V/V % of base carrying liquid molecule; the opaque microstructure has a thickness of 10 nm~1000 nm; and/or a graph code contained in each magnetic microchip comprises at least one group of two-dimensional graphs formed by combining at least two opaque microstructures; two-dimensional graphs contained in at least two different magnetic microchips are geometrically distinguished.

5. The preparation method according to claim 1, wherein the step of machining the ferrofluid layer to form an opaque microstructure as the graph code comprises: providing a patterned etch mask on the ferrofluid layer and etching the ferrofluid layer to form the opaque microstructure.

6. The preparation method according to claim 5, comprising: etching the ferrofluid layer by adopting machining, a dry etching process or a wet etching process, thereby forming the opaque microstructure.

7. The preparation method according to claim 1, wherein:
the transparent substrate layer is formed on a sacrificial layer;
providing the sacrificial layer on a base,
uniformly coating the film formed by the ferrofluid on the transparent substrate layer.

8. The preparation method according to claim 7, comprising: after the opaque microstructure is wrapped with a transparent material, removing the sacrificial layer to obtain more than two pieces of magnetic microchips independent from each other.

9. The preparation method according to claim 8, comprising: dissolving and removing the sacrificial layer with a reagent capable of dissolving the sacrificial layer.

10. The preparation method according to claim 7, comprising: forming a metal thin layer as the sacrificial layer on the base through a metal plating process; the material of the metal thin layer comprising aluminum.

11. The preparation method according to claim 1, wherein, the transparent material wrapping the opaque microstructure has a visible light transmittance of 50% or more; the transparent material wrapping the opaque microstructure has a thickness of 100 nm~5000 nm; the material of the transparent substrate layer and the transparent material are selected from bioinert transparent materials.

12. The preparation method according to claim 1, wherein, any one of length, width and height or a diameter of the magnetic microchip is 1 μm~1000 μm; the magnetic microchip has a flat two-dimensional surface-shaped structure.

13. A preparation method of more than two magnetic microchips having a graph code, comprising the following steps:
forming a transparent substrate layer on a sacrificial layer, wherein the sacrificial layer is on a base;
uniformly coating a film formed by ferrofluid on the transparent substrate layer;
at least removing a portion of base carrying liquid in the film so that at least a portion of the film is cured to form a ferrofluid layer;
providing a patterned etch mask on the ferrofluid layer, and etching the ferrofluid layer to form an opaque microstructure as the graph code;
wrapping the opaque microstructure with a transparent material to form a magnetic microchip, dividing the magnetic microchip, and then removing the sacrificial layer to obtain more than two pieces of magnetic microchips independent from each other.

14. The preparation method according to claim 1, also comprising: connecting a capture substance for specifically capturing a target substance on an exterior surface of the opaque microstructure; the capture substance being selected from an organic compound and/or an inorganic compound; the organic compound comprising any one or a combination of more than two of protein, an antibody, a polypeptide and nucleic acid.

15. The preparation method according to claim 1, also comprising: connecting a hydrophilic group on a surface of the opaque microstructure; the source substance of the hydrophilic group comprising any one or a combination of more than two of PEG, glucan, chitosan and alginate.

16. A magnetic microchip having a graph code, comprising:
the graph code comprising more than one opaque microstructure mainly consisting of colloid aggregates formed by aggregating magnetic solid particles, wherein adjacent magnetic solid particles are isolated at least by an organic molecule and/or an inorganic molecule;
and a transparent encapsulating material at least used for wrapping the opaque microstructure.

17. The magnetic microchip having a graph code according to claim 16, wherein, the graph code comprises at least one group of two-dimensional graphs formed by combining at least two opaque microstructures; all the opaque microstructures in each magnetic microchip are combined to form one group of two-dimensional graphs; the two-dimensional graphs contained in at least two different magnetic microchips are geometrically distinguished.

18. The magnetic microchip having a graph code according to claim 17, wherein, the magnetic microchip has a flat two-dimensional surface-shaped structure.

19. The magnetic microchip having a graph code according to claim 17, wherein, the opaque microstructure is formed by the ferrofluid after at least a portion of base carrying liquid is removed; the organic molecule and/or the inorganic molecule comprises a surfactant molecule and/or a base carrying liquid molecule derived from the ferrofluid; the ferrofluid comprises magnetic solid particles, a surfactant and a base carrying liquid, the base carrying liquid being sufficient to cooperate with the surfactant to disperse the magnetic solid particles to form colloid suspension; the magnetic solid particle has a particle size of 1 nm~1000 nm; the ferrofluid comprises any one or a combination of more than two of ferrite series ferrofluid, metal series ferrofluid and ferric oxide series ferrofluid; wherein the material of the ferrite series ferrofluid comprises any one or a combination of more than two of $Fe_3O_4$, $\gamma\text{-}Fe_2O_3$ and $MeFe_2O_4$, wherein, Me is at least selected from Co, Ni, Mn or Zn; the metal series ferrofluid comprises metal microparticles formed by any one or a combination of more than two of Ni, Co and Fe.

20. The magnetic microchip having a graph code according to claim 19, wherein, in the opaque microstructure, adjacent magnetic solid particles are isolated at least by an organic molecule and/or an inorganic molecule derived from the ferrofluid; the organic molecule and/or the inorganic molecule comprises a surfactant molecule and/or a base carrying liquid molecule derived from the ferrofluid; the opaque microstructure contains 50V/V %~99V/V % of magnetic solid particles, 0.5V/V %~50V/V % of surfactant molecule and 0.5V/V %~50V/V % of base carrying liquid molecule.

21. The magnetic microchip having a graph code according to claim 17, wherein, any one of length, width and height or a diameter of the magnetic microchip is 1 μm~1000 μm; the magnetic microchip has a flat two-dimensional surface-shaped structure; and/or the opaque microstructure has a thickness of 10 nm~1000 nm.

22. The magnetic microchip having a graph code according to claim 17, wherein, the transparent encapsulating material wrapping the opaque microstructure has a visible light transmittance of 50% or more; the transparent encapsulating material wrapping the opaque microstructure has a thickness of 100 nm~5000 nm; the transparent encapsulating material is selected from bioinert transparent materials.

23. The magnetic microchip having a graph code according to claim 17, wherein, the surface of the magnetic microchip is also connected with a capture substance for specifically capturing a target substance; the capture substance is selected from an organic compound and/or an inorganic compound; the organic compound comprises one or a combination of more than two of protein, an antibody, a polypeptide and nucleic acid.

24. The magnetic microchip having a graph code according to claim 17, wherein, the surface of the magnetic microchip is also connected with a hydrophilic group; the source substance of the hydrophilic group comprises any one or a combination of more than two of PEG, glucan, chitosan and alginate.

25. A substance analysis method, comprising:
providing a magnetic microchip having a graph code according to claim 17;
connecting at least one capture substance on the magnetic microchip, the capture substance being capable of specifically capturing a corresponding target substance;
dispersing the magnetic microchip into a liquid phase system which might contain the target substance, and keeping the magnetic microchip suspended in the liquid phase system;
capturing the target substance which might be present in the liquid phase system by the capture substance;
taking the magnetic microchip out of the liquid phase system through action of a magnetic field, and imaging in an optical channel having a set wavelength to determine whether the magnetic microchip has the capture substance or not and/or quantitatively analyzing the concentration of the target substance in the liquid phase system.

26. The substance analysis method according to claim 25, comprising: keeping the magnetic microchip suspended in the liquid phase system at least through mechanical agitation or action of an alternating magnetic field.

27. The substance analysis method according to claim 25, wherein, the liquid phase system also contains a labeling substance indicating whether the capture substance reacts with the target substance or not; the capture substance and/or the target substance is modified with the labeling substance.

28. The substance analysis method according to claim 25, wherein, the optical channel having a set wavelength is selected from any one or a combination of more than two of a transmission optical channel, a reflection optical channel, a fluorescence channel and a chemiluminiscence channel.

\* \* \* \* \*

SEQUENCE LISTING

```
<160> NUMBER OF SEQ ID NOS: 6

<210> SEQ ID NO 1
<211> LENGTH: 60
<212> TYPE: DNA
<213> ORGANISM: Artificial Sequence
<220> FEATURE:
<223> OTHER INFORMATION: HPV16

<400> SEQUENCE: 1
aaaaaaaaaa aaatctcacc tcccacctct gtcattatgt gctgccatat ctacttcaga     60

<210> SEQ ID NO 2
<211> LENGTH: 60
<212> TYPE: DNA
<213> ORGANISM: Artificial Sequence
<220> FEATURE:
<223> OTHER INFORMATION: HPV18

<400> SEQUENCE: 2
aaaaaaaaaa aaatctcacc tcccacctct atatgtgctt ctacacagtc tcctgtacct     60

<210> SEQ ID NO 3
<211> LENGTH: 60
<212> TYPE: DNA
<213> ORGANISM: Artificial Sequence
<220> FEATURE:
<223> OTHER INFORMATION: HPV31
```

```
<400> SEQUENCE: 3
aaaaaaaaaa aaatctcacc tcccacctct caatatgtct gtttgtgctg caattgcaaa        60

<210> SEQ ID NO 4
<211> LENGTH: 60
<212> TYPE: DNA
<213> ORGANISM: Artificial Sequence
<220> FEATURE:
<223> OTHER INFORMATION: HPV33

<400> SEQUENCE: 4
aaaaaaaaaa aaatctcacc tcccacctct tgactttatg cacacaagta actagtgaca        60

<210> SEQ ID NO 5
<211> LENGTH: 60
<212> TYPE: DNA
<213> ORGANISM: Artificial Sequence
<220> FEATURE:
<223> OTHER INFORMATION: HPV58

<400> SEQUENCE: 5
aaaaaaaaaa aaatctcacc tcccacctct aaatatgtct gtgtgttctg ctgtgtcttc        60

<210> SEQ ID NO 6
<211> LENGTH: 60
<212> TYPE: DNA
<213> ORGANISM: Artificial Sequence
<220> FEATURE:
<223> OTHER INFORMATION: HBB

<400> SEQUENCE: 6
aaaaaaaaaa aaatctcacc tcccacctct gacattatgc actgaagtaa ctaaggaagg        60
```